(12) United States Patent
Buchholz et al.

(10) Patent No.: US 6,685,924 B2
(45) Date of Patent: *Feb. 3, 2004

(54) CONJUGATE, ITS PREPARATION AND USE

(75) Inventors: Herwig Buchholz, Frankfurt am Main (DE); Ralf Anselmann, Ramsen (DE); Hansjuergen Driller, Gross-Umstadt (DE); Michael Kirschbaum, Weiterstadt (DE); Frank Pflücker, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 64 days.

This patent is subject to a terminal disclaimer.

(21) Appl. No.: 10/010,142

(22) Filed: Nov. 7, 2001

(65) Prior Publication Data

US 2002/0150600 A1 Oct. 17, 2002

(30) Foreign Application Priority Data

Nov. 9, 2000 (DE) .......................... 100 55 469

(51) Int. Cl.$^7$ .............................. A61K 7/42; A61K 7/44; A61K 7/00
(52) U.S. Cl. ........................... 424/59; 424/60; 424/400; 424/401
(58) Field of Search ........................... 424/59, 60, 400, 424/401

(56) References Cited

U.S. PATENT DOCUMENTS

| | | | | |
|---|---|---|---|---|
| 5,252,323 A | * | 10/1993 | Richard et al. | ............... 424/59 |
| 5,601,811 A | * | 2/1997 | Gallagher et al. | .......... 424/709 |
| 5,882,632 A | * | 3/1999 | Allard et al. | ................. 424/59 |

\* cited by examiner

*Primary Examiner*—Shelley A. Dodson
(74) *Attorney, Agent, or Firm*—Jenkens, Wilson & Taylor, P.A.

(57) ABSTRACT

The invention relates to a conjugate which can be used for preparing dermatological and cosmetic compositions. The invention also relates to processes for preparing such conjugate and to its use.

36 Claims, No Drawings

CONJUGATE, ITS PREPARATION AND USE

DESCRIPTION

1. Technical Field

The present invention relates to a conjugate, which can be used for the preparation of dermatological and cosmetic compositions. The invention also relates to processes for preparing such conjugate and to its use.

2. Related Art

Dermatological or cosmetic compositions are used for example to protect skin against harmful external effects, such as against sun radiation. In modern society a more or less marked tanning of skin is considered to be attractive and an expression of dynamics and sportiveness. Besides this desired effect of sun on skin also a series of undesired side effects is occurring such as sunburn or premature aging of skin and wrinkling. Meanwhile a number of efficient UV filters has been developed which, applied onto the skin in the form of creams, lotions or gels, can inhibit effectively the development of sunburn even under a more intensive exposure to sun. The UV filters contained in the pharmaceutical or cosmetic preparations form a film and a layers respectively, on the surface of the skin. The known UV filters and sun protecting agents act in such manner that they absorb certain parts of sunlight so that this radiation cannot penetrate into deeper layers of the skin. It is known that the most dangerous part of the sun radiation is formed by the ultraviolet rays having a wavelength of less than 400 nm. The lower limit of the ultraviolet rays which reach the surface of earth by the absorption in the ozone layer is restricted to about 280 nm. The sun filters commonly used in the cosmetics absorb in a wavelength range of from 280 to 400 nm. This range comprises UVB rays having a wavelength between 250 and 320 nm which play a decisive roll in the formation of a sun erythema, as well as UVA rays having a wavelength between 320 and 400 nm which cause tanning but also aging of skin, promote the initiation of an erythematic reaction or increase this reaction with certain individuals or even may initiate phototoxic or photoallergic and irritative reactions.

Light protection formulations which have been applied onto the skin have the purpose to hold back skin damaging parts of radiation. As light filters inorganic or organic materials can be used.

Light protection formulations based on organic light filters contain organic light filters which are soluble in water and/or oil or are soluble neither in water nor in oil.

Light protection formulations having insoluble particulate organic light filters are described for example in WO 97/3643. The group of insoluble organic light filters is, however, restricted to a few classes of compounds.

Light protection formulations having organic light filters and being soluble in water and/or oil are described in publications DE-A-197 46 654, DE-A-197 55 504, EP-A-709 080, EP-A-775 698, EP-A-893 119 and U.S. Pat. No. 5,882,632.

In DE-A-197 46 654 the use of 4,4-diaryl-butadiene derivatives as soluble organic light filters in light protection formulations for protecting the skin against UVA radiation is described.

The above mentioned light protection formulations must contain the organic light filters in a high concentration in order to ensure a sufficient light protection. However, the most serious disadvantage of organic soluble light filters consists in that optionally they penetrate into the skin due to their solubility and can cause skin damages or allergies.

In JP-A-11-255 630 a light protection formulation for protecting the skin against UVA radiation is described which contains a dibenzoyl methane derivative and is applied to a silicone polymer-coated inorganic support. However, the preparation of this light protection formulation is troublesome and time consuming due to a multitude of operations. Furthermore, dibenzoyl methane derivatives are not photostable (light-resistant).

Dermatological and cosmetic compositions can further contain a multitude of active substances, such as organic substances having antioxidative and/or radical inhibiting properties as well as repellents.

In general, a heterogenisation of the active substances contained in dermatological and cosmetic compositions is desirable, since i.a. a penetration into the skin and a possibly resulting skin damage or allergy can be prevented.

SUMMARY OF THE INVENTION

It is an object of the present invention to provide a conjugate based on organic active substances and which cannot penetrate into the skin.

This object is achieved according to the present invention by providing a conjugate which comprises an inorganic pigment and an active substance based on organic compounds, the active substance being covalently bound through a spacer group to the inorganic pigment. The conjugate of the invention is characterized in that the spacer group contains a silicon atom or an aluminum atom.

The invention also provides a dermatological or cosmetic composition comprising at least one conjugate of the above mentioned type and at least one cosmetically, pharmaceutically and/or dermatological compatible vehicle and/or adjuvant.

In the frame of the present invention the expression "conjugate" means a product which is obtained by a molecular i.e. covalent bond between the active substance and the inorganic pigment. The expression "active substance" comprises for example light absorbing organic compounds, substances having antioxidative and/or radical inhibiting properties, repellants, preservatives and derivatives of these active substances which can be bound covalently through a spacer group to an inorganic pigment. The active substance or derivative thereof comprises preferably a nucleophilic group. It is preferred that the active substance per se, i.e. without being bound to an inorganic pigment is water soluble and/or oil soluble.

The conjugate of the invention contains an inorganic pigment. In the frame of the present invention the expression "pigment" means a dye (colorant) or filler being insoluble in the application medium. The inorganic pigment in the conjugate of the invention preferably is a metal oxide or a semi-metal oxide.

Examples of inorganic pigments comprise oxides, silicates, phosphates, carbonates, sulfates and nitrides, oxides being preferably used.

Preferred inorganic pigments comprise magnesium oxide, aluminum oxide, silicon dioxide, zinc oxide, cerium oxide, titanium dioxide, zirconium oxide, manganese oxide, boron oxide, red or black iron oxide, talc, kaolin, natural and synthetic mica materials, such as muscovite, phlogopite, lepidolite, biotite and vermiculite, magnesium carbonate, calcium carbonate, aluminum silicate, barium silicate, calcium silicate, magnesium silicate, strontium silicate, barium sulfate, calcium sulfate, calcium phosphate, fluoroapatite, hydroxyapatite, ceramic powder, boron nitride, iron titanate, zeolite and mixtures thereof. Silicon dioxide, titanium dioxide, mica, talc and mixtures of the above mentioned pigments (in the following called "mixed pigments") such as silicon dioxide/titanium dioxide are particularly preferably used.

Commercially available inorganic mixed pigments which can be used according to the invention comprise mixtures of titanium dioxide/mica, titanium dioxide/micaltin oxide, titanium dioxide/mica/iron oxides, titanium dioxide/mica/silicon dioxide, titanium dioxide/mica/carmine, mica/iron oxides/aluminum oxide, mica/iron oxides, titanium dioxide/mica/zinc oxide, titanium dioxide/mica/barium sulfate, mica/silicon dioxide and titanium dioxide/iron oxides/silicon dioxide. These mixed pigments are sold under the names Timiron®, Soloron®, Colarona®, Dichrona®, Microna®, Micronaspher® and Ronaspher®.

Light scattering pigments such as Ronaspher® LDP as well as nacreous pigments can also be used.

The silicates can have a chain, belt or sheet-shaped structure. Silicates having a sheet-shaped structure such as mica or talc are preferably used.

The form in which the metal odor semi-metal compound is present, is not restricted to certain forms.

The metal or semi-metal compound has preferably the form of spherical particles. Suitable materials based on silicon dioxide comprise commercially available products offered under the name Monospher®, such as Monospher® 10 (silicon dioxide having a particle size of 10 nm), Monospher® 25 (silicon dioxide having a particle size of 25 nm), Monospher® 100 (silicon dioxide having a particle size of 100 nm) or Monospher® 500 (silicon dioxide having a particle size of 500 nm), or Ronaspher® (silicon dioxide having a particle size of from 50 nm to 3 $\mu$m).

The preparation of monodisperse spherical oxide particles is known. According to the process described in EP-A-216 278 monodisperse spherical oxide particles can be obtained by hydrolytic polycondensation of alkoxides.

Other preferred forms in which the metal or semi-metal compounds can be present comprise needles and flocs.

DETAILED DESCRIPTION OF THE INVENTION

The active substances based on organic compounds which according to the invention are bound covalently to an inorganic pigment comprise for example light absorbing organic compounds, substances having antioxidative and/or radical inhibiting properties, repellants as well as preservatives. However, the active substances used according to the invention are not limited to these active substances.

The light absorbing organic compounds are selected from compounds which absorb UV light. Compounds are used which absorb UV light in the UVB range, i.e. in the range of from 280 to 320 nm and/or in the UVA range, i.e. in the range of from 320 to 400 nm.

UVB filters preferably exhibit a maximum of absorption in the range of from 300 to 320 nm and they can be selected from known substandes already described in the literature. Examples comprise derivatives of aminobenzoic acid, cinnamic acid, salicylic acids benzylidene camphor, phenyl benzimidazole, diphenyl-acrylate, triazine, triazole and vinyl group-containing amides.

Examples of aminobenzoic acid derivatives comprise 4-aminobenzoic acid, 4-aminobenzoic acid-2,3-dihydroxypropyl ester, 4-[bis(2-hydroxypropyl)-amino] benzoic acid ethylester, 4-(dimethylamino)benzoic acid-2-ethylhexylester (e.g. Eusolex® 6007) and ethoxylated 4-aminobenzoic acid ethylester (e.g. Uvinul® P25).

Examples of cinnamic acid derivatives comprise cinnamic acid esters like p-methoxy-cinnamic acid-2-ethylhexylester (e.g. Eusolex® 2292), 4-methoxy-cinnamic acid isopentylester, e.g. in the form of a mixture of the isomers (e.g. Neo Heliopan® E 1000) and 4-methoxy-cinnamic acid-2-methylhexylester, as well as the diethanolamine salt of 4-methoxy-cinnamic acid and cinnamic acid derivatives as described in U.S. Pat. No. 5,601,811 and in WO 97/851.

The salicylic acid derivatives include for example 2-ethylhexyl salicylate (e.g. Eusolex® OS), 4-isopropyl-benzylsalicylate (e.g. Megasol®) and 3,3,5-trimethylcyclohexyl-salicylate (e.g. Eusolex® HMS).

Examples for benzylidene camphor derivatives comprise 3-(4'-methyl-benzylidene)-dl-camphor (e.g. Eusolex® 6300), 3-benzylidene camphor (e.g. Mexory® SD), polymers of N-{(2- and 4)-[(2-oxoborn-3-ylidene)methyl]-benzyl}-acrylamide (e.g. Mexoryl® SW), N,N,N-trimethyl-4-(2-oxoborn-3-ylidenemethyl)anilinium methylsulfate (e.g. Mexoryl® SK) and $\alpha$-(2oxo-born-3-ylidene)toluene-4-sulfonic acid (e.g. Mexoryl® SL).

As examples of phenylbenzimidazole derivatives 2-phenylbenzimdazole-5-sulfonic acid and its potassium, sodium and triethanolamine salts can be mentioned (e.g. Eusolex® 232).

Special examples of diphenylacrylate derivatives comprise 2-cyano-3,3'-di-phenylacrylic acid-2-ethylhexylester and 2-cyano-3,3'-diphenylacrylic acid ethylester.

Examples of triazole derivatives comprise benzotriazoles, such as 2-(2-hydroxy-5-methylphenyl) benzotriazole as well as the triazoles described in EP-A-893 119.

Special examples of triazines comprise 2,4,6-tri-{4-[(2-ethylhexyl)oxycarbonyl]-phenylamino}-1,3,5-triazine as well as the compounds described in EP-A-893 119. Further examples comprise trianiline-triazine derivatives as disclosed in U.S. Pat. No. 5,332,568, EP-A-570 838, EP-A-517 104, U.S. Pat. No. 5,252,323, WO 93/17002 and WO 97/03642, hydroxyphenyltriazine derivatives as described in EP-A-775 698 as well as bis-resorcinol-dialkylaminotriazines as disclosed for example in EP-A-780 382.

Preferred examples of vinyl groups containing amide derivatives comprise those described in EP-A-893 119.

As UVA filter substances preferably compounds can be used which exhibit a maximum of absorption in the range of from 330 to 360 nm. Any known UVA filter substances like derivatives of benzophenone, dibenzoylmethane, diarylbutadiene and triazine can be used.

Special examples of benzophenone derivatives comprise 2-hydroxy-4-methoxybenzophenone (e.g. Eusolex® 4360), 2-hydroxy4-methoxybenzophenone-5-sulfonic acid and its sodium salt (e.g. Uvinul® MS-40), as well as 8-(2,2'-dihydroxy-4-meothxybenzophenone).

Special examples of benzoylmethane derivatives and dibenzoylmethane derivatives comprise 1-(4-tert-butylphenyl)3-(4-methoxyphenyl)-propane-1,3-dione (e.g. Eusolex® 9020) and 4-isopropyidibenzoylmethane (e.g. Eusolex® 8020).

Examples of diarylbutadiene derivatives comprise the 4,4-diarylbutadienes described in DE-A-197 46 654, in particular 4,4-diphenylbutadiene.

Special examples of triazines comprise 2,4-bis-{[4-(2-ethylhexyloxy)-2-hydroxy]-phenyl}-6-(4-methoxyphenyl)-1,3,5-triazine.

Further suitable UV filters comprise 2-cyano-3,3-diphenylacrylic acid-2-ethylhexylester (e.g. Eusolex® OCR), 3,3'-(1,4-phenylenedimethylene)-bis-(7,7-dimethyl-2oxobicyclo-[2.2.1]hept-1-ylmethanesulfonic acid and its salts (e.g. Mexoryl® SX), 2,4,6-trianilino-(p-carbo-2'-ethylhexyl-1'-oxy)-1,3,5-triazine (e.g. Uvinul® T 150), 2-(2H-benzotriazole-2-yl)4-methyl-6-(2-methyl-3-(1,3,3,3-tetramethyl-1-(trimethylsilyloxy)disiloxanyl)propyl)-phenol (e.g. Silatrizole®), 4,4'-[(6-[4-((1,1-dimethyl-ethyl) aminocarbonyl)-phenylamino]-1,3,5-triazine-2,4-diyl) diimino]bis(benzoic acid-2-ethylhexylester) (e.g. Uvasorb® HEB), α-(trimethylsilyl)-ω-[trimethylsilyl)oxy]poly[oxy-(dimethyl [and about 6% methyl[2-[p-[2,2-bis (ethoxycarbonyl]vinyl]phenoxy]-1-methylene-ethyl] and ca, 1.5% methyl[3-[p-[2,2-bis(ethoxycarbonyl)vinyl) phenoxy)-propenyl) and 0.1 to 0.4% (methylhydrogen] silylene]] (n≈60) (CAS-No. 207 574-74-1), 2,2'-methylene-bis-(6-(2H-benzotriazole-2-yl)4-(1,1,3,3-tetramethylbutyl) phenol) (CAS-No. 103 597-45-1), 2,2'-(1,4-phenylene)-bis-(1H-benzimidazole-4,6-disulfonic acid, monosodium salt) (CAS-No. 180 898-37-7) and 2,4-bis-{[(2-ethyl-hexyloxy)-2-hydroxyl]-phenyl}-6-(4-methoxy-phenyl)-1,3,5-triazine (CAS-No. 103 597-45-, 187 393-00-6).

Preferred UV radiation absorbing organic compounds are 3-(4'-methyl-benzylidene)-dl-camphor, 1-(4-tert-butylphenyl)-3-(4-methoxyphenyl)-propane-1,3-dione, 4-isopropyl-dibenzoylmethane, 2-hydroxy-4-methoxy-benzophenone, methoxycinnamic acid octylester, methoxy-cinnamic acid octylester, 3,3,5-trimethylcyclohexyl-salicylate, 4-(dimethylamino)-benzoic acid-2-ethylhexylester, 2-cyano-3,3-diphenylacrylic acid-2-ethylhexylester, 2-phenylbenzimidazole-5-sulfonic acid as well as its potassium, sodium and triethanolamine salts.

Photostable UV radiation absorbing organic compounds are preferably used, photostabile UVA filters and UVB filters being particularly preferably used.

Suitable substances having antioxidative and/or radical inhibiting properties comprise for example flavonoides, coumaranones, amino acids (e.g. glycine, histidine, tyrosine, tryptophane) and derivatives thereof, imidazoles, (e.g. uro-caninic acid) and derivatives thereof, peptides such as D,L-camosine, D-camosine, L-camosine and derivatives thereof (e.g. anserine), carotinoides, carotines (e.g. α-carotine, β-carotine, lycopine) and derivatives thereof. chlorogenic acid and derivatives thereof, liponic acid and derivatives thereof (e.g. dihydroliponic acid), aurothioglucose, propy-lthiouracile and other thiols (e.g. thioredoxine, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), diaurylthiodipropionate, distearylthiodipropionate, thio-dipropionic acid and derivatives thereof (esters, ethers, peptides, lipides, nucleotides and nucleosides) as well as sulfoximine compounds (e.g. buthionine sulfoximines, homocysteine sulfoximine, buthionine sulfones, penta, hexa, heptathionine sulfoximine), chelating agents (e.g. α-hydroxy fatty acids, palmitic acid, phytinic acid, lactoferrin), α-hydroxy acids (e.g. citric acid, lactic acid, malic acid), huminic acid, gailic acid, gall extracts, bilirubin, biliverdin, EDTA, EGTA and derivatives thereof, unsatur-ated fatty acids and derivatives thereof, vitamin C and derivatives (e.g. ascorbyl palmitate, ascorbyl acetate), toco-pheroles and derivatives (e.g. vitamin E acetate), vitamin A and derivatives (e.g. vitamin A palmitate) as well as coniferyl benzoate of benzoic resin, rutinic acid and deriva-tives thereof, α-glycosylrutin, ferula acid, furfurylidene glucitol, carnosine, butylhydroxytoluene, butylhydroxyanisol, nordohydroguajaretic acid, trihydroxybutyrophenone, quercitin, ureic acid and deriva-tives thereof, mannose and derivatives thereof vitamin E and derivatives thereof, stilbenes and derivatives thereof (e.g. stilbene oxide, trans-stilbene oxide) as well as BHT (2,6-di-tert-butyl-4-methyl-phenol).

Preferred antioxidants comprise flavonoides, coumaranones, vitamins and BHT.

The glucosides of flavanones, flavones, 3-hydroxyflavones (=flavanoles), aurones, isoflavones and rotenoides are considered as flavanoides (Römpp Chemie Lexikon, Vol. 9, 1993). However, in the frame of the present invention they also comprise the aglycones, i.e. the sugar-free components and the derivatives of flavonoides and aglycones. In the frame of the present invention the couma-ranones also comprise their derivatives.

Preferred flavonoides are derived from flavanones, flavones, 3-hydroxyflavones, aurones and isoflavones, in particular from flavanones, flavones, 3-hydroxyflavones and aurones.

The flavanones are characterized by the following basic structure:

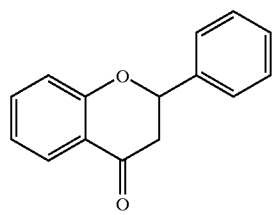

The flavones are characterized by the following basic structure:

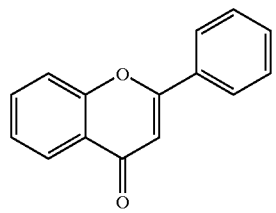

The 3-hydroxyflavones (flavonoles) are characterized by the following basic structure:

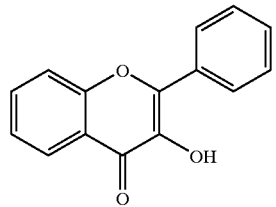

The isoflavones are characterized by the following basic structure:

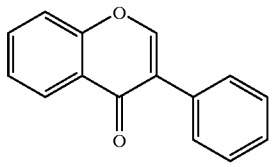

The aurones are characterized by the following basic structure:

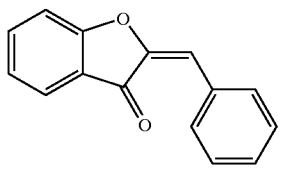

The coumaranones are characterized by the following basic structure:

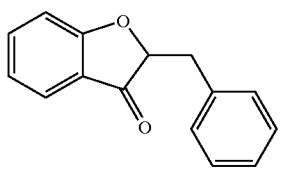

Preferably the flavonoides and coumaranones are selected from the compounds of formula (1):

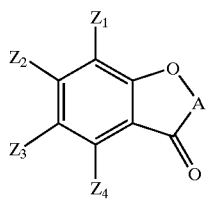

(1)

wherein $Z_1$ to $Z_4$ independently each represent H, OH, alkoxy, hydroxyalkoxy, mono- or oligoglycoside radicals, wherein the alkoxy and hydroxyalkoxy groups can be branched and straight and contain from 1 to 18 carbon atoms and wherein also sulfate or phosphate can be bound to the hydroxy groups of the named radicals, A is selected from the group consisting of the partial formulae (1A), (1B) and (1C)

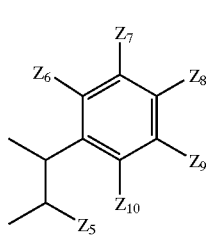

(1A)

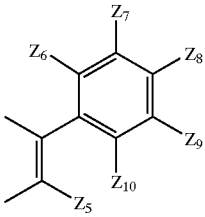

(1B)

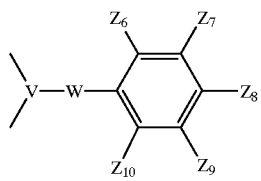

(1C)

$Z_5$ represents H, OH or OR,

R represents a mono- or oligoglycoside radical, $Z_6$ to $Z_{10}$ have the meanings of the radicals $Z_1$ to $Z_4$ and

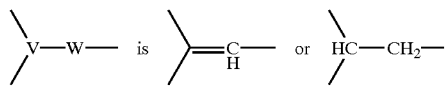

The alkoxy groups are preferably linear and contain from 1 to 12, preferably from 1 to 8 carbon atoms. These groups thus correspond to the formula —O—$(CH_2)_m$—H, wherein m ist 1,2,3,4,5,6,7 or 8 and in particular 1 to 5.

The hydroxyalkoxy groups are preferably linear and contain from 2 to 12, preferably from 2 to 8 carbon atoms. These groups thus correspond to the formula —O—$(CH_2)_n$—OH, wherein n is 2,3,4,5,6,7 or 8, in particular 2 to 5 and particularly preferred 2.

The mono- and oligoglycoside radicals preferably are constituted of 1 to 3 glycoside units. Preferably these units are selected from the group consisting of hexosyl radicals, in particular rhamnosyl radicals and glucosyl radicals. But also other hexosyl radicals, for example allosyl, altrosyl, galactosyl, gulasyl, idosyl, mannosyl and talosyl can be optionally used with advantage. It can also be advantageous to use pentosyl radicals.

In a preferred embodiment $Z_1$ and $Z_3$ represent H, $Z_2$ and $Z_4$ have another meaning than H, in particular represent OH, methoxy, ethoxy or 2-hydroxyethoxy, $Z_5$ represents H, OH or a glycoside radical being constituted of 1 to 3, preferably 1 or 2 glycoside units, $Z_6$, $Z_9$ and $Z_{10}$ represent H and $Z_7$ and $Z_8$ have another meaning than H, in particular represent OH, methoxy, ethoxy or 2-hydroxyethoxy.

Particularly preferred compounds are represented by the following general formula:

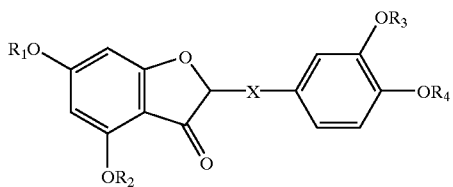

wherein
—X— represents a single bond, —CH$_2$— or =CH— and
R$_1$, R$_2$, R$_3$ and R$_4$ which can be identical or different, independetly represent H,
straight or branched C$_1$–C$_{12}$-alkyl groups and/or -alkylcarbonyl groups,
straight or branched C$_3$–C$_{12}$-alkenyl groups and/or -alkenylcarbonyl groups,
straight or branched C$_1$–C$_{12}$-hydroxyalkyl- and/or -hydroxyalkylcarbonyl groups wherein the hydroxy group can be bound to a primary or secondary carbon atom of the chain and wherein the alkyl chain can also be interrupted by oxygen,
C$_3$–C$_{10}$-cycloalkyl- and/or -cycloalkylcarbonyl groups and C$_3$–C$_{12}$-cycloalkenyl- and/or -cycloalkenylcarbonyl groups wherein the rings can also be bridged (linked) by —(CH$_2$)$_n$-groups wherein n is 1 to 3,
aryl groups and/or arylcarbonyl groups heteroaryl groups and/or heteroarylcarbonyl groups,
wherein these groups can be substituted by alkyl, hydroxy, alkoxy, amino, mono- and dialkylamino, sulfonic acid, carboxylic and/or halogen groups,
mono- or oligoglycoside radicals,

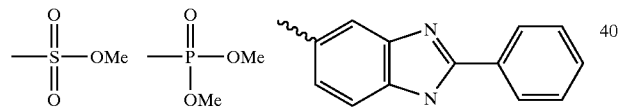

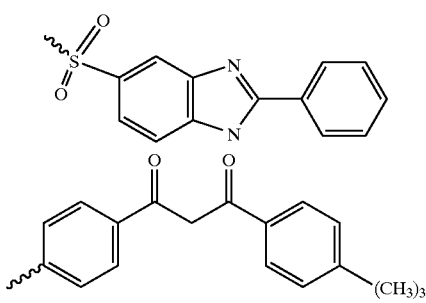

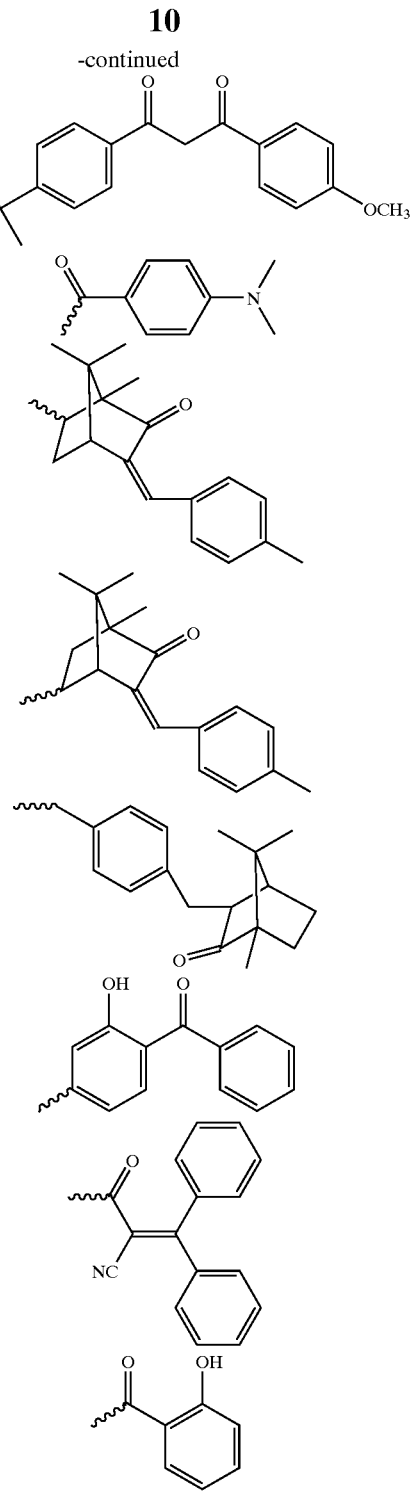

wherein R$^5$ represents tert, -butyl or isopropyl and
Me represents a proton or an alkaline metal ion, in particular a potassium ion.

The radicals thus can be bound to the basic body as ethers or as esters.

In a further preferred embodiment the flavonoides are selected from the following compounds, 4,6,3',4'-tetrahydroxyauron, quercetin, rutin, isoquercetin, anthocyanidin (cyanidin), eriodictyol, taxifolin, luteolin, trishydroxyethylquercetin (troxequercetin), trishydroxyethylrutin (troxerutin), trishydroxyethylisoquercetin (troxeisoquercetin) as well as trishydroxyethylluteolin (troxeluteolin).

Preferred flavonoides are in particular rutin and troxerutin. Particularly preferred is troxerutin.

Preferred among the coumaranones is 4,6,3',4'-tetrahydroxybenzyl-coumaranone-3.

Suitable repellants comprise amides and derivatives thereof, in particular N,N-diethyl-3-methyl-benzamide, 3-[N-n-butyl-N-acetyl]-aminopropionic acid ethylester (IR3535®) and N,N-caprylic acid diethylamide (IR790®).

Suitable preservatives comprise benzalkonium chloride, benzoic acid and salts thereof (such as sodium benzoate), methylparaben, ethylparaben, propylparaben, sorbic acid and salts thereof (such as potassium sorbate), cetylpyridinium chloride, cetrimonium chloride as well as salicylic acid and salts thereof (such as sodium salicylate).

The active substance used according to the invention can also be an antiphlogistic substance.

The active substance used according to the invention preferably is soluble in oil and/or water and by the covalent bond to an inorganic pigment it is transferred into a condition in which it can no more penetrate into the skin.

Preferred conjugates of the invention are represented by the following general formula:

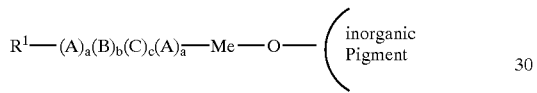

wherein:
- $R^1$ represents the covalently bound active substance-group,
- A represents O, S or NH,
- B represents a straight or branched alkylene group having up to 20, preferably from 1 to 12, particularly preferably from 3 to 12 carbon atoms,
- C represents a straight or branched alkyleneoxy group having up to 20, preferably from 1 to 12, particularly preferably from 3 to 12 carbon atoms, wherein the oxygen atom of the alkyleneoxy group is bound to group B,
- Me represents a silicon atom or an aluminum atom.
- a represents 0 or 1,
- b represents 0 or 1 and
- c represents 0 or 1.

The silicon atom and aluminum atom, respectively, can form one or more covalent bonds to the inorganic pigment and/or to the active substance-group.

Preferred examples of $R^1$ comprise, besides the above named substances:

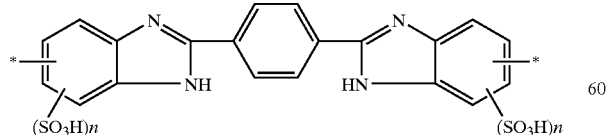

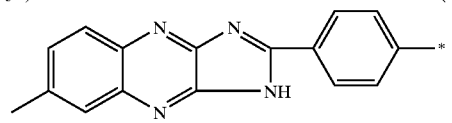

-continued

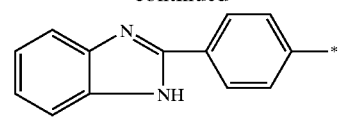

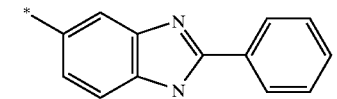

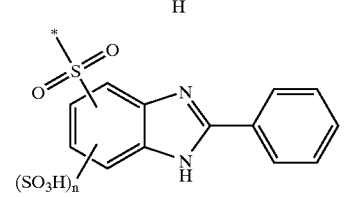

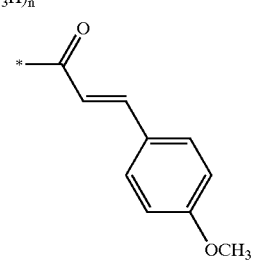

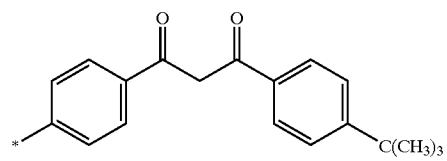

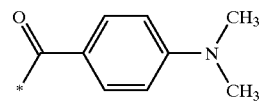

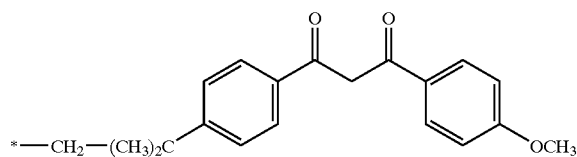

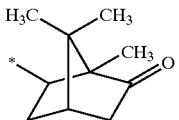

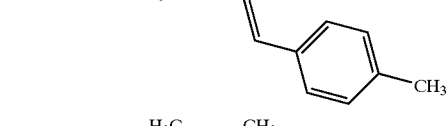

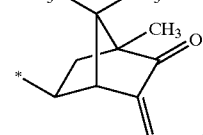

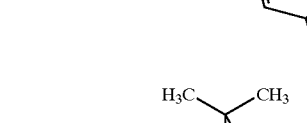

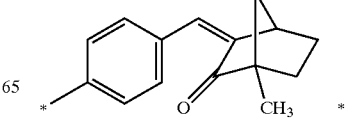

-continued

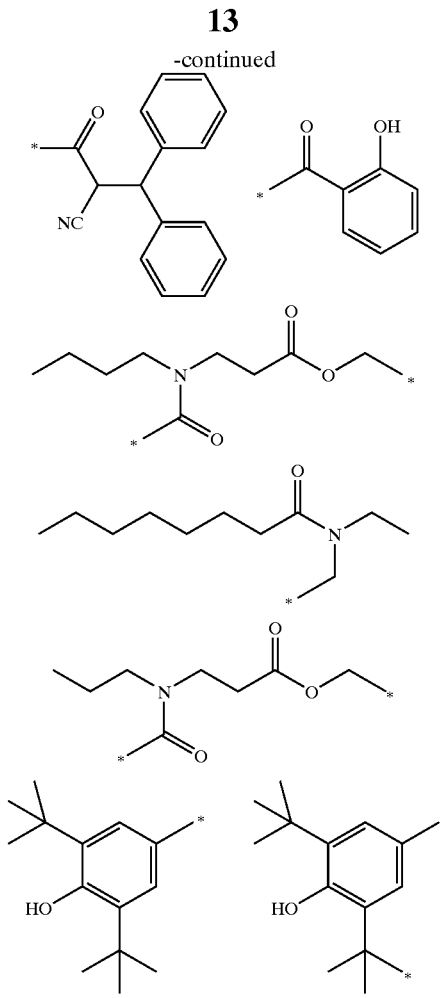

wherein n is 0, 1 or 2 and * is a bond to the spacer group.

In the following the preparation of the conjugate of the invention is described.

For preparing the conjugate of the invention the active substance is covalently bound through a spacer group (linking group) to an inorganic pigment. In the frame of the present invention the expression "spacer group" means a monomeric or oligomeric compound group, however, no polymeric group.

The spacer group is preferably a linking group represented by the following formula:

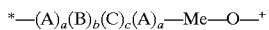

*—(A)$_a$(B)$_b$(C)$_c$(A)$_a$—Me—O—+ wherein:

A represents O, S or NH,

B represents a straight or branched alkylene group having up to 20, preferably from 1 to 12, particularly preferably from 3 to 12 carbon atoms, C a straight or branched alkyleneoxy group having up to 20, preferably from 1 to 12, particularly preferably from 3 to 12 carbon atoms, wherein the oxygen atom of the alkyleneoxy group is bound to group B, Me represents a silicon atom or an aluminum atom, a is 0 or 1, b is 0 or 1, c is 0 or 1,

* represents the bond to the active substance-group and

+ represents the bond to the inorganic pigment.

The conjugate of the invention can be prepared by first reacting a compound having a silicon atom or an aluminum atom and containing at least two terminal reactive groups with the active substance based on organic compounds in order to covalently bind both compounds through one of the two reactive groups. The obtained intermediate product then is reacted with the inorganic pigment in order to covalently bind the intermediate product through the other reactive group to an inorganic pigment.

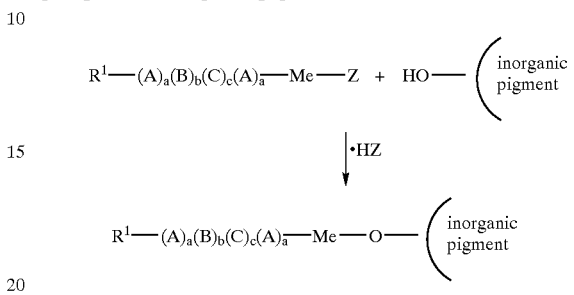

wherein Z represents a group which can be split off, for example a halogen atom (preferably Cl) or an alkoxy group.

Examples of the active substance-group $R^1$ comprise the groups mentioned above.

1-(4-tert-Butylphenyl)-3-(4-allyloxyphenyl)propane-1,3-dione (a Eusolex® 9020 analogue), for example, can be reacted with triethoxysilane as follows:

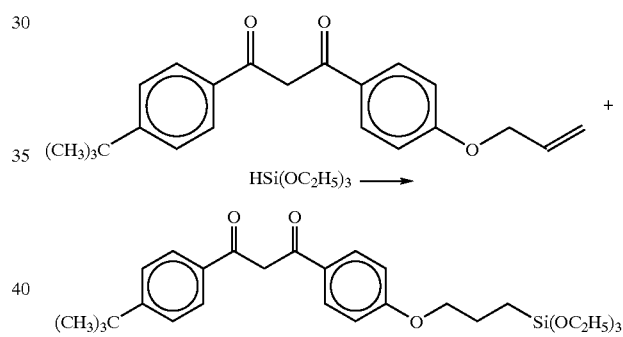

The silylated intermediate product then is covalently bound to an inorganic pigment such as silicon dioxide. The ethoxy groups of the intermediate product react with the hydroxy groups bound to the surface of the silicon dioxide by splitting off ethanol.

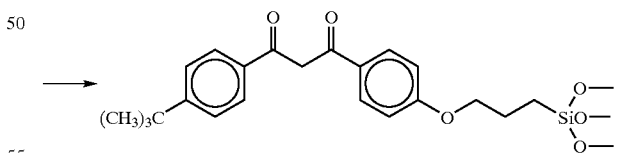

This variant has the advantage that the intermediate products can be purified and thus a higher chemical purity of the final product can be obtained.

Alternatively, the conjugate of the invention can be prepared by first reacting a compound having a silicon atom or an aluminum atom and containing at least two terminal reactive groups with an inorganic pigment in order to covalently bind the compound and the pigment through one of both reactive groups. The obtained intermediate product then is reacted with the active substance based on organic substances in order to covalently bind the intermediate product through the other reactive group to the active substance. This variant has preparative advantages (starting with high excesses of reagents, easy recovery etc.).

It is also possible to bind at first the inorganic pigment to suitable, commercially available silicon compounds. In this way a multitude of differently functionalized particles can be obtained. Lateron the single functionalities can be used to form the conjugates.

In this way the following conjugates for example can be obtained: (in the following formulae the group R represents an alkyl group and the group X represents a group which can be split off).

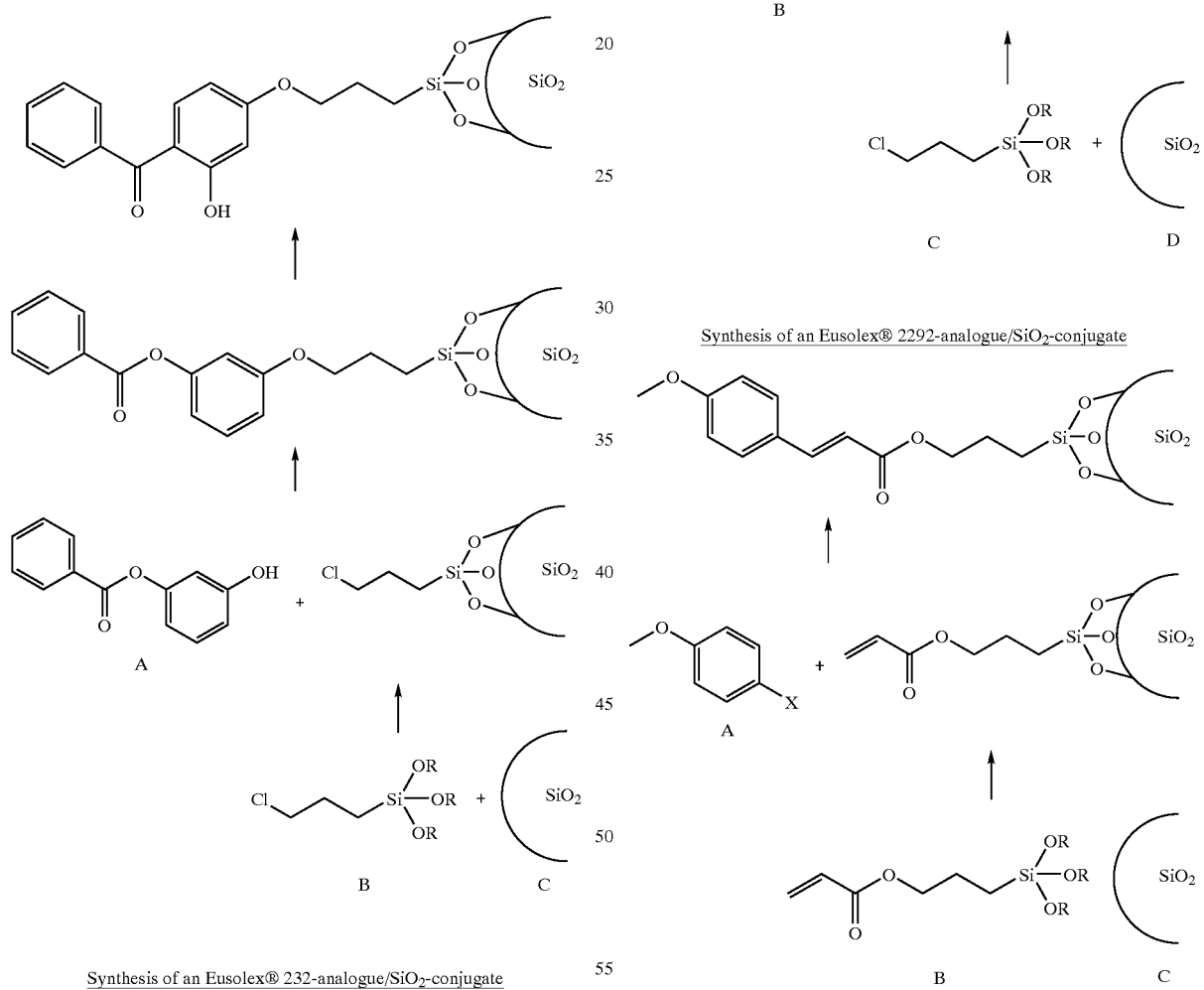

Alternatively, in a first step the coupling of A with B can be carried out. In a second step then it can be bound to the inorganic pigment.

The synthesis of the conjugate of the invention is carried out in an inert solvent which is selected dependent on the used starting materials. If for example an alkoxysilane is used, the corresponding alcohol is preferably used as the solvent.

The number of the reactive groups, such as hydroxy groups, at the surface of the inorganic pigment can be increased by the process described in DE-A-198 02 753.

Inorganic support materials depending on the chemical structure exhibit at the surface a more or less large number of reactive OH groups which can form a chemical bond. This number is for example about 4.4 to $8.5/nm^2$ for completely hydroxylated $SiO_2$ monospheres (H. P. Boehm. "Angew. Chem." 78, 617 (1966)). These values were confirmed by J. Kratochvila et al., "Journal of Non-Crystalline Solids" 143, 14–20 (1992). At a bonding distance of about 0.16 nm for the Si—O bond and at an angle of 150° for the Si—O—Si angle there are about 13 Si atoms/$nm^2$ at the surface of the $SiO_2$ monospheres. This means, that in the superficial monolayer a maximum of 13 Si—OH groups can be present with an additional triple valence bonding of the Si through the oxidic oxygen bridges. However, normally in $SiO_2$ monospheres which have been dried at room temperature, only 4 Si—OH groups can be expected (see Boehm and Kratochvila).

In order to obtain an number of active Si—OH groups as large as possible on the $SiO_2$ monospheres per weight unit the surfaces of the $SiO_2$ monospheres can be increased in the form of pores, gaps and/or by particle diameters which are as small as possible. By increasing the number of the Si—OH groups by saturating with water or steam no sufficient solution is obtained, since the water additionally adsorbed at the surface causes hydrolysis of most of the chemisorptive bonds of the surface to ligands. On the other hand, intensive drying leads to a decrease of the number of the Si—OH groups to lower than 2 per $nm^2$.

According to the process described in DE-A-198 02 753 for example an oxide or silicate in an inert aprotic solvent such as THF, DMF, cyclohexane or toluene is treated with a strongly basic reagent such as an alkaline metal or alkaline earth metal hydroxide, a hydride or an alcoholate in order to split the superficial oxide bondings of the oxide or silicate, and then the treated oxide or silicate is treated with an inorganic or organic acid to form additional hydroxy groups.

When inorganic pigments used according to the invention are treated according to this process, the bond density of the active substances to the surface of the inorganic pigment can be increased.

The particle size of the conjugate of the invention is not limited to a certain particle size; normally, however, it lies within a range of from 1 nm to 250 $\mu$m, preferably in a range of from 1 nm bis 1 $\mu$m and particularly preferably in a range of from 5 nm to 100 nm, in order to ensure an optimal distribution on the skin.

The conjugate of the invention can be dried after its preparation and then it can be introduced into the dermatological or cosmetic composition or it can be introduced into the dermatological or cosmetic composition in the form of a dispersion, for example dispersed in a cosmetic oil or liquid light filter.

Suitable oil components comprise natural and synthetic substances like paraffin oil, glycerylstearate, isopropylmyristate, diisopropyladipate, 2-ethylhexanoic acid-acetylstearylester, hydrogenated polyisobutene, vaseline, caprylic acid/caprlnic acid-triglycerides, microcrystalline wax, lanolin, mineral oils, mineral waxes, esters of fatty acids with alcohols like isopropanol, propyleneglycol or glycerine, alkylbenzoates, silicone oils like dimethylpolysiloxanes, diethylpolysiloxanes or diphenylpolysiloxanes, stearic acid, light filters which are present in liquid form as well as vitamin K1. Preferred examples comprise ethylbutylacetylaminopropionate (IR 3535™), butyleneglycol-dicaprylate/dicaprinate (Miglyol 8810), propyleneglycol-dicaprylate/dicaprinate, $C_{12-15}$-alkyibenzoates, isopropylmyristate, caprylic acid/caprinic acid-triglycerides, octylpalmitate, almond oil, avocado oil, jojoba oil, isostearylisostearate, octyldodecanol, dibutyladipate (Cetiol B), coco acid-glycerides (Myritol 331), dicaprilylether (Cetiol OE), isostearyl-neopentanoate (Ceraphyl 375), $C_{12-15}$-alkyllactates (Ceraphyl 41), diortylmalate (Ceraphyl 45) as well as the liquid light filters Eusolex® 2292, Eusolex® OCR, Eusolex® 6007, Eusolex® HMS and Eusolex® OS.

The dermatological or cosmetic composition of the invention contains the conjugate described above or a combination of the conjugates described above with at least one cosmetically, pharmaceutically and/or dermatologically compatible vehicle and/or adjuvant. Of course, the dermatological or cosmetic composition can also contain the conjugate of the invention in combination with other active substances like organic or inorganic UVA and UVB filters, IR or VIS filters. Particularly preferred is the combination with further UV filters comprising the unbound light filters described above or mixtures thereof. The ratio between the bound active substances (i.e. the active substances which are bound to pigments) and the unbound active substances (i.e. the active substances which are not bound to pigments) preferably lies within a range of from 1:10 to 10:1 and particularly preferred in a range of from 1:5 to 5:1. For example, light filters bound to pigments can be combined with unbound light filters.

The dermatological or cosmetic composition of the invention contains the conjugate of the invention optionally in combination with further cosmetic substances, preferably in an amount in the range of from 0.05 to 30% by weight, particularly preferred in an amount in the range of from 0.5 bis 10% by weight and especially preferred in an amount in the range of from 0.6 to 6% by weight, based on the total weight of the dermatological or cosmetic composition.

Definitions of the Cosmetic Substances

Examples of inorganic UV filters comprise coated titanium dioxide (e.g.

Eusolex® T-2000 or Eusolex® T-AQUA), zinc oxides (e.g. Sachtotec®), iron oxides and cerium oxides. These inorganic UV filters are incorporated into the dermatological or cosmetic compositions of the invention usually in an amount of from 0.5 to 10% by weight, preferably from 2 to 5% by weight.

Examples of vehicles and adjuvants comprise thickening agents, softening agents, humectants, surfactants, emulgators, preservatives, antifoaming agents, perfumes, fats and waxes, lanolin, propellants, stabilizers, antioxidants, bactericides, dyes and/or pigments which color the formulation per se or the skin, film forming agents, odor improvers, complexing agents and other usual additives used in cosmetics.

As dispersant and solubilizer, respectively, a cosmetic oil, a wax or another fatty body, an alcohol or a polyol or mixtures thereof can be used. Particularly preferred alcohols or polyols are ethanol, i-propanol, propylenglycol. glycerine and sorbitol.

As emulgators preferably known W/O emulgators, but also O/W emulgators like polyglycerine esters, sorbitane esters or partially esterified glycerides can be used.

Typical examples of fats comprise glycerides and as waxes for example bees wax, carnauba wax, paraffin wax or microwaves can be used, optionally in combination with hydrophilic waxes.

As stabilizers metal salts of fatty acid like magnesium, aluminum and/or zinc stearate can be used.

Suitable thickening agents are for example cross-linked polyacrylic acids and derivatives thereof, polysaccharides, in particular xanthan gum, guar-guar, agar-agar, alginates and tyloses, carboxymethylcellulose and hydroxyethylcellulose, further fatty alcohols, monoglycerides and fatty acids, polyacrylates, polyvinylalcohol and polyvinylpyrrolidons.

Usable film forming agents comprise hydrocolloides, such as chitosan, microcrystalline chitosan or quaternary chitosan, polyvinylpyrrolidone, vinylpyrrolidone-vinylacetate copolymers, polymers of the acrylic acid series, quaternary cellulose derivatives and similar compounds.

Suitable preservatives are for example formaldehyde solutions, p-hydroxy-benzoate or sorbic acid.

As nacreous agents for example glycoldistearic acid esters such as ethylene-glycol-distearate, but also fatty acids and fatty acid monoglycolesters are usable.

As dyes substances which are suitable and admitted for cosmetic purposes can be used as listed for example in the publication "Kosmetische Färbemittel" of the Farbstoffkommission der Deutschen Forschungsgemeinschaft, published in Verlag Chemie, Weinheim, 1984.

As antioxidants for example amino acids, imidazoles, peptides, carotinoides, α-hydroxy acids, unsaturated fatty acids, vitamin A, C and/or E and suitable derivatives of these substances can be used as well as zinc and its compounds (like ZnO, $ZnSO_4$) or selenium and its compounds (like selenium methionine). Preferred antioxidants comprise the substances mentioned above having antoxidative properties, where flavonoides, coumaranones, vitamins and BHT are preferred.

Mixtures of antioxidants can also be used in the dermatological and cosmetic compositions of the invention. Known and commercially available mixtures comprise mixtures which contain as active ingredients lecithin, L-(+)-ascorbylpalmitate and citric acid (e.g. Oxynex® AP), natural tocopherols, L-(+)-ascorbylpalmitate, L-(+)-ascorbic acid and citric acid (e.g. Oxynex® K LIQUID), tocopherol extracts from natural sources, L-(+)-ascorbylpalmitate, L-(+) ascorbic acid and citric acid (e.g. Oxynex® L LIQUID), DL-α-tocopherol, L-(+)-ascorbylpalmitate, citric acid and lecithin (e.g. Oxynex® LM) or BHT, L-(+)-ascorbylpalmitate and citric acid (e.g. Oxynex® 2004).

In a preferred ambodiment the flavonoides are selected from the following compounds: 4,6,3',4'-tetrahydroxyauron, quercetin, rutin, isoquercetin, anthocyanidin (cyanidin), eriodictyol, taxifolin, luteolin, trishydroxyethylquercetin (troxequercetin), trishydroxyethylrutin (troxerutin), trishydroxyethyl-isoquercetin (troxeisoquercetin), trishydroxyethylluteolin (troxeluteolin) as well as sulfates and phosphates.

Among the flavonoides rutin and troxerutin are particularly preferred. Especially preferred is troxerutin.

Among the coumaranones 4,6,3',4'-tetrahydroxy-benzylcoumaranone-3 as well as it salts (sulfate, phosphate) are preferred.

The dermatological or cosmetic composition of the invention can contain as further ingredients vitamins. Preferably vitamins and vitamin derivatives selected from vitamin A, vitamin A propionate, vitamin A palmitate, Vitamin A acetate, retinol, vitamin B, thiaminechloride-hydrochloride (vitamin $B_1$), riboflavin (vitamin $B_2$), nicotic acid amide, vitamin C (ascorbic acid), vitamin D, ergocalciferol (vitamin $D_2$), vitamin E, DL-α-tocopherol, tocopherol E acetate, tocopherol-hydrogensuccinate, vitamin $K_1$, esculin (active substance of vitamin P), thiamine (vitamin $B_1$), nicotinic acid (niacin), pyridoxin, pyridoxal, pyridoxamine, (vitamin $B_6$), panthothenic acid, biotin, folic acid and cobalamin (vitamin $B_{12}$), are contained in the dermatological or cosmetic compositions of the invention, particularly preferred are vitamin A palmitate, vitamin C, DL-α-tocopherol, tocopherol E acetate, nicotinic acid, pantothenic acid and biotin.

Optionally the dermatological or cosmetic compositions of the invention can also contain one oder more chemical substances having self-tanning properties.

As chemical substances having self-tanning properties all natural and synthetic substances which are suitable for the preparation of cosmetic formulations and which ate known to the expert can be used. These can be both plant extracts and synthetic self-tanning agents like dihydroxyacetone or α-ketoles as well as erythrolose.

Application forms of the dermatological or cosmetic compositions of the invention comprise: suspensions, emulsions, fat sticks, pastes, ointments, creams or milk (O/W, W/O, O/W/O, W/O/W), lotions, powders, soaps, tenside containing cleansing preparations, oils, aerosols, sprays as well as oily-alcoholic, oily-aqueous or aqueous-alcoholic; gels and solutions, respectively. Further application forms are for example sticks, shampoos and shower baths.

The aqueous phase of the dermatological or cosmetic compositions of the invention preferably contains alcohols, diols or polyols as well as ethers, preferably ethanol, isopropanol, 1,2-propandiol, propyleneglycol, glycerine, ethyleneglycol, ethyleneglycolmonoethyl- or -monobutylether or analogous products, further one or more thickener, such as silicon dioxide, aluminum silicates, polysaccharides and derivatives thereof, e.g. hyaluronic acid, xanthan gum, hydroxypropylmethylcellulose or a polyacrylate selected from the group of the so-called carbopoles.

Usable oil components comprise the oil components described above.

Ointments, pastes, creams and gels can contain usual vehicles such as animal and plant fats, waxes, paraffins, starch, tragacanth, cellulose derivatives, polyethylene glycols, silicones, bentonites, silicic acid, talc and zink oxide or mixtures of these substances.

Powders and sprays can contain usual vehicles such as milk sugar, talc, silicic acid, aluminum hydroxide, calcium silicate and polyamide powder or mixtures of these substances. Sprays can additionally contain usual propellants, such as chlorfluorohydrocarbons, propane/butane or dimethylether.

Solutions and emulsions can contain usual vehicles such as solvents, solubilizers and emulgators, e.g. water, ethanol, isopropanol, ethylcarbonate, ethylacetate, benzylalcohol, benzylbenzoate, propylene glycol, 1,3-butylglycol, oils, in particular cotonseed oil, peanut oil, cornseed oil, olive oil, castor oil and sesame oil, glycerine fatty acid esters, polyethylene glycols and fatty acid esters of sorbitan or mixtures of these substances.

Suspensions can contain usual vehicles such as liquid diluents, e.g. water, ethanol or propylene glycol, suspending agents like ethoxylated isostearyl alcohols, polyoxyethylene sorbitolesters and polyoxyethylene sorbitanesters, microcrystalline cellulose, aluminum-meta-hydroxide, bentonite, agar-agar and tragacanth or mixtures of these substances.

Soaps can contain usual vehicles like alkali salts of fatty acids, salts of fatty acid semi-esters, fatty acid proteinhydrolysates, isothionates, lanolin, fatty alcohol, plant oils, plant extracts, glycerine, sugars or mixtures of these substances.

Tenside containing cleansing products can contain usual vehicles such as salts of fatty alcohol sulfates, fatty alcohol ethersulfates, sulfosuccinic acid semi-esters, fatty acid proteinhydrolysates, isothionates, imidazolinium derivatives, methyltaurates, sarcosinates, fatty acid amide-ethersulfates, alkylamido-betaines, fatty alcohols, fatty acid glycerides, fatty acid diethanolamides, plant oils and synthetic oils, lanolin derivatives, ethoxylated glycerine fatty acid esters or mixtures of these substances.

Face and body oils can contain usual vehicles such as synthetic oils like fatty acid esters, fatty alcohols, silicone oils, natural oils like plant oils and oily plant extracts, paraffin oils, lanolin oils or mixtures of these substances. Preferred examples of such verhicles comprise the oil components mentioned above.

In a preferred embodiment the dermatological or cosmetic composition according to the invention is an emulsion being present in the form of a protection cream or milk and comprising in addition to the conjugate of the invention fatty alcohols, fatty acids, fatty acid esters, in particular triglycerides of fatty acids, lanolin, natural or synthetic oils or waxes and emulgators in the presence of water.

Further preferred embodiments are oily lotions based on natural or synthetic oils and waxes, lanolin, fatty acid esters, in particular triglycerides of fatty acids or oily-alcoholic lotions based on alcohols like ethanol or on glycols like propylene glycol and/or on polyols like glycerine and oils, waxes and fatty acid esters like triglycerides of fatty acids.

The dermatological or cosmetic composition of the invention can also have the form of an alcoholic gel containing one or more alcohols or polyols like ethanol, propylene glycol or glycerine and a thickener like diatomaceous earth, The oily-alcoholic gels can further contain a natural or synthetic oil or wax.

The solid sticks can contain natural or synthetic waxes and oils, fatty alcohols, fatty acids, fatty acid esters, lanolin and other fat bodies.

In the dermatological or cosmetic composition of the invention confectionated as an aerosol, generally usual propellants like alkanes, fluoroalkanes and chlorofluoroalkanes are used.

Further typical cosmetic application forms comprise lip sticks, lip care sticks, rouge, powder, emulsion and wax make-up as well as pre-sun and after-sun preparations.

All vehicles and adjuvants which can be used in the dermatological or cosmetic compositions of the invention are either known and commercially available or can be synthesized according to known processes.

The dermatological or cosmetic compositions of the invention can contain the vehicles and adjuvants mentioned above each in an amount in the range of from 0.001 to 30% by weight, preferably in an amount in the range of from 0.05 to 20% by weight and particularly preferably in an amount in the range of from 1 to 10% by weight.

The dermatological or cosmetic composition of the invention can be prepared by using processes which are known to an expert.

The conjugate of the invention can also be used to protect the skin, in particular to protect the Langerhans cells in the skin, to protect the DNA or to provide immunoprotection.

The conjugate of the invention can be used not only in cosmetics but also for example for the preparation of varnishes or security markings. In this case for example the group $R^1$ in the general formula mentioned above can be a fluorescent group which can be excited by UV light.

The following examples illustrate the invention. The used starting materials are either commercially available or can be synthesized in a known manner.

EXAMPLE

Example 1

Preparation of a Eusolex® 9020/Monospher® 100 Conjugate

A Eusolex® 9020/Monospher® 100-conjugate has been prepared according to the following reaction scheme:

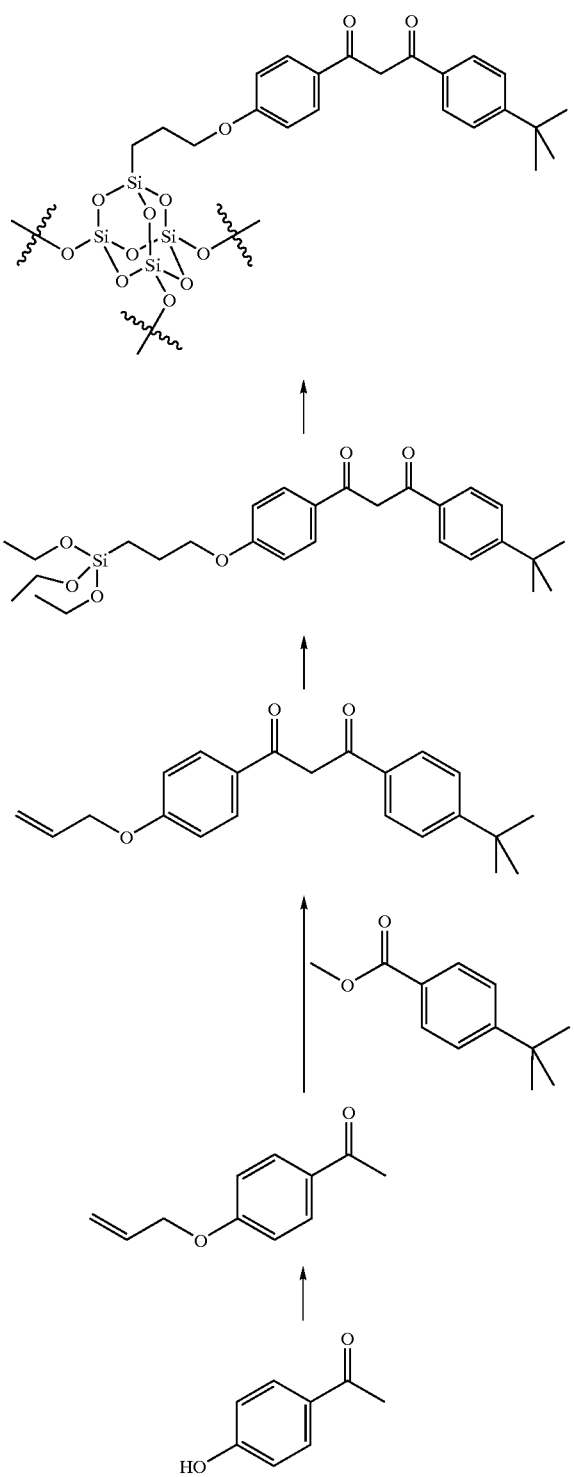

Preparation of 4-(2-propenyloxy)-acetophenone (1. Realization)

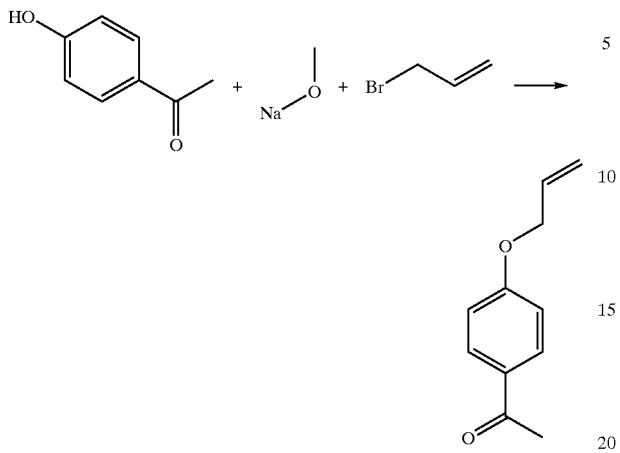

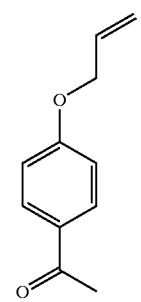

The apparatus used for carrying out the reaction was flushed with nitrogen in order to displace the air in the apparatus. Then 116 g of methanol and 16.67 g of 4-hydroxyacetophenone were added to the apparatus. The mixture was stirred until a homogeneous solution has been obtained. Then 24.85 g of sodium methylate (30% solution in methanol) was added dropwise within 10 minutes and after an exothermic reaction a reddish solution was obtained. Then the solution was heated to 52° C. and within a period of 12 minutes 16.31 g of 3-bromo-1-propene were added dropwise. The reaction mixture was then maintained for 15 hours at a temperature of from 63 to 64° C.

The yellow reaction solution was cooled to 32° C. and the methanol was removed in a rotary evaporator. The obtained partially crystalline concentrate was added with 120 g of toluene and 50 g of deionized water. Then it was stirred for 10 minutes.

After the phase separation the organic phase was concentrated azeotropically in a rotary evaporator to form a yellow oil.

Yield; 22.89 g of raw product.

The raw product was distilled at an air bath temperature of 116 to 118° C. in vacuum (0.7 to 0.9 mbar) to obtain 18.71 g of distillate. The distillate was distilled once more at 115° C. in vacuum (0.7 to 0.9 mbar) to obtain 18.10 g of 4-(2-propenyloxy)acetophenone.

Preparation of 4-(2-pronenyloxy)-acetophenone (2. Realization)

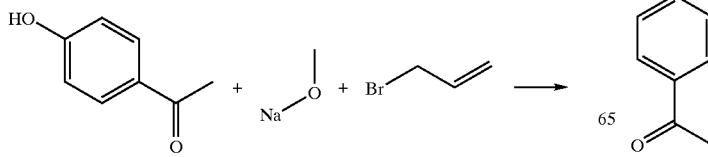

The apparatus used for carrying out the reaction was flushed with nitrogen to displace the air in the apparatus. Then 116 g of methanol and 16.67 g of 4-hydroxyacetophenone were introduced into the apparatus. The mixture was stirred until a homogeneous solution has been obtained. Then 27 g of sodium methylate (30% solution in methanol) was added dropwise within 8 minutes to obtain, after an exothermic reaction, a reddish solution. Then the solution was heated to 55° C. and thereafter 17.77 g of 3-bromo-1-propene were added dropwise within a period of 16 minutes. The reaction mixture was maintained at a temperature of from 63 to 64° C. for 14.75 hours.

The yellow reaction solution was cooled to 28° C. and the methanol was removed in a rotary evaporator. The obtained partially crystalline concentrate was added with 120 g of toluene and 50 g of deionized water. Thereafter it was stirred for 5 minutes.

After the phase separation the organic phase was washed with 20 ml of a sodium hydroxide solution (1-molar) and washed twice with each 25 g of deionized water and then concentrated azeotropically to a yellow oil in a rotary evaporator.

Yield: 20.1 g of raw product.

The raw product was distilled at an air bath temperature of 116 to 116° C. in vacuum (0.6 to 0.7 mbar) to obtain 18.56 g of 4(2-propenyloxy)-acetophenone.

Preparation of an Analogue of Eusolex® 9020 Capable to be Coupled (1. Realization)

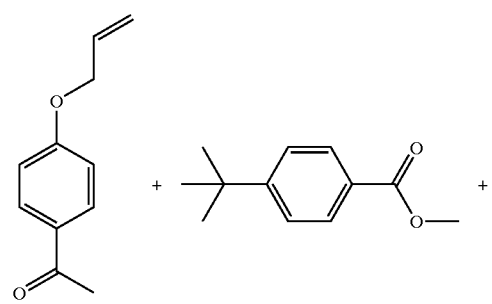

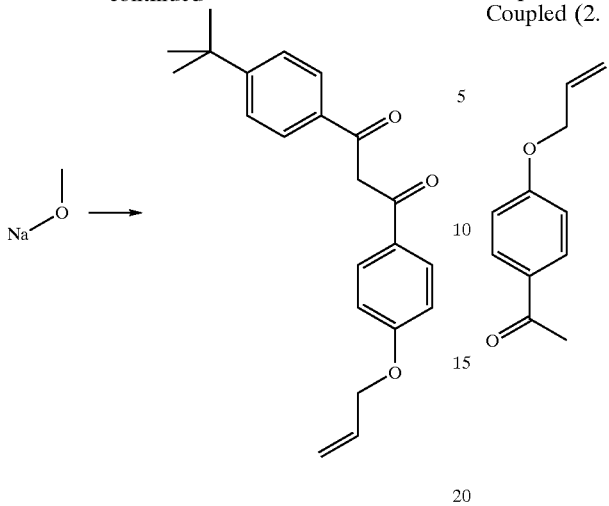

The apparatus used for carrying out the reaction was flushed with nitrogen and the air in the apparatus was displaced. Then 268 g of cyclohexane were added and heated to 48° C. within 15 minutes. Thereafter 27.03 g of sodium methylate (30% solution in methanol) were added dropwise within 2 minutes. The emulsion was heated to 64° C. and then a solution of 27.9 g of 4-t-butylbenzoic add methylester in 35 g of cyclohexane was added dropwise within 9 minutes. The reaction mixture was stirred for 20 minutes until a reaction temperature of 80.5° C. had been reached. During this period 40 ml of a cyclohexane/metbanol mixture formed in a water separator were removed in portions. Then a solution of 17.64 g of 4-(2-propenyloxy)acetophenone in 36 g of cydohexane was added dropwise within 60 minutes. During this time and in the following 60 minutes each 10 to 15 ml of the cyclohexane/methanol mixture (in total 70 ml) were removed in intervals of each 20 minutes. The reaction temperature was 75 to 80° C. Thereafter 84 g of cyclohexane were added dropwise within further 2.5 hours. Occasionally a cyclohexane/methanol mixture (a total of 80 ml) were removed in portions. The reaction mixture was vigorously stirred for a total of 7.5 hours.

Then the suspension was cooled to 70° C. and thereafter a mixture of 36 g of acetic acid (100%) and 30 g of deionized water was added dropwise and stirred for 10 minutes.

After the phase separation at 50° C. the organic phase was washed twice with 50 g and 20 g, respectively, of deionized water and then azeotropically concentrated to a red-brown oil in a rotary evaporator.

Yield: 42.9 g of raw product.

The raw product was distilled at an air bath temperature of 118 to 133° C. in vacuum (0.5 to 0.7 mbar) to obtain 13.36 g of a distillate and 29.22 g of a distillation residue.

The distillation residue was dissolved under heating (50 to 60° C.) in 50 g of 2-propanol, filtered on adsorbent cotton and cooled under stirring. After the addition of seed crystals a crystallization occurred (30 to 40° C.).

After stirring for 60 minutes at room temperature the suspension was cooled slowly to 4 to 6° C. within further 60 minutes. The crystallizate was isolated, washed in portions with cold 2-propanol and dried by suction. The drying was carried out in a vacuum exsiccator at 35° C.

Yield: 23–89 g of crystallizate (Eusolex® 9020-analogue capable to be coupled) melting point of the crystallizate: 65 to 67° C.

Preparation of an Analogue of Eusolex® 9020 Capable to be Coupled (2. Realization)

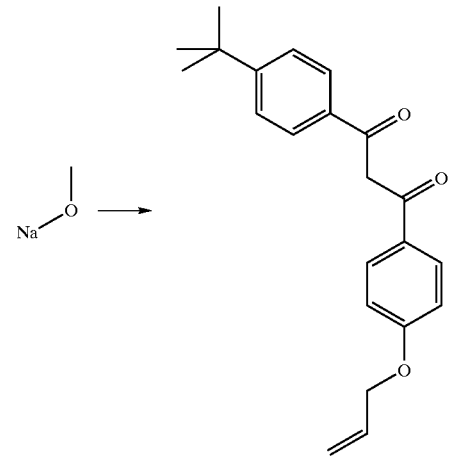

The apparatus used for carrying out the reaction was flushed with nitrogen and the air in the apparatus was displaced. Then 119 g of cyclohexane were added and heated to 40° C. within is minutes. Thereafter 13.5 g of sodium methylate (30% solution in methanol) were added dropwise within 2 to 3 minutes. The emulsion was heated to 70° C. and then within a period of 8 minutes a solution of 14.02 g of 4-t-butylbenzoic acid methylester in 25 g of cyclohexane was added dropwise. The reaction mixture was stirred ed for 12 minutes at 79° C. During this period twice each 20 ml of a cyclohexane/methanol mixture formed within the water separator were removed in portions. Then within a period of 25 minutes a solution of 8.81 g of 4-(2-propenyloxy)-acetophenone in 25 g of cyclohexane was added dropwise. The inhomogeneous reaction mixture was vigorously stirred at a bath temperature of 95 to 100° C. and the temperature of the reaction mixture decreased within 75 minutes to 75° C. After removing again the cyclohexane/methanol mixture the temperature of the reaction mixture increased to 80° C. The reaction mixture was vigorously stirred for further 4.75 hours at 79 to 82° C. During this period five times a cyclohexane/methanol mixture was removed and 126 g of cyclohexane were added dropwise.

Then the suspension was cooled to 70° C. and thereafter a mixture of 18 g of acetic acid (100%) and 15 g of deionized water was added dropwise and then stirred for 10 minutes.

After the phase separation at 50° C. the organic phase was washed twice with 50 g and 20 g respectively, of deionized water and then azeotropically concentrated to a brown oil in a rotary evaporator.

Yield: 21.4 g of raw product.

The raw product was distilled in vacuum (0.6 to 0.8 mbar) at an air bath temperature of 115 to 133° C. to obtain 5.89 g of a distillate and 15.30 g of a distillation residue.

The distillation residue was dissolved in 30 g of 2-propanol while heating (50 to 60° C.), filtered on adsorbent cotton and cooled while stirring. After the addition of seed crystals a crystallization occurred (30 to 40° C.).

After stirring for further 60 minutes at room temperature the suspension was cooled slowly within 45 minutes to 10° C. The crystallizate was isolated, washed with cold 2-propanol in portions and dried by suction. The drying was carried out in a vacuum exsiccator at 35° C.

Yield: 11,35 g of crystallizate (Eusolex® 9020-analogue capable to be coupled), melting point of the crystallizate: 66.5 to 68° C.

Recrystallization 33.5 g of the crystallizate obtained above were dissolved under heating (60 to 70° C.) in 84 g of 2-propanol. The solution was filtered on absorbent cotton and cooled while stirring. After the addition of seed crystals a crystallization occurred (44 to 45° C.).

After stirring for 2.5 hours at room temperature the crystallizate was isolated, washed with 2-propanol in portions, dried by suction and dried in a vacuum exsiccator at 35° C.

Yield: 29.90 g of crystallizate (melting point: 67.1° C.)

Preparation of a Silanized Eusolex® 9020-analogue

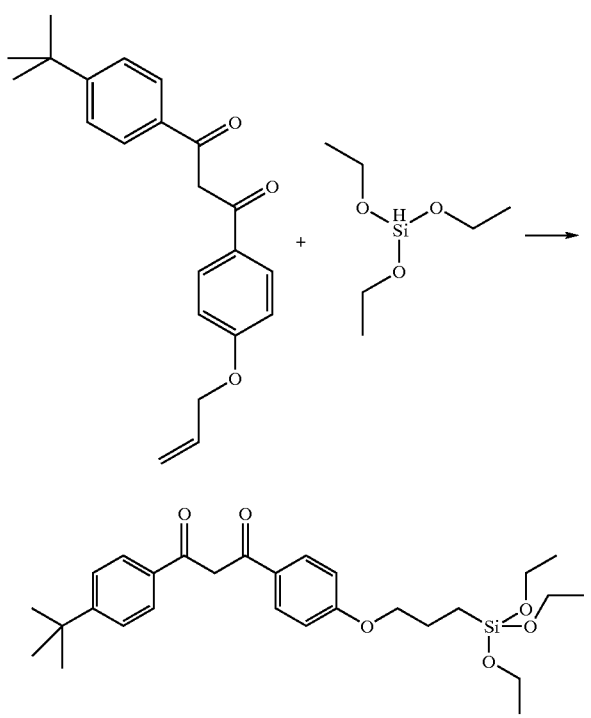

The apparatus used for carrying out the reaction was flushed with nitrogen and the air in the apparatus was displaced. Then 11.21 g of the crystallizate were dissolved in the apparatus in 7.98 g of THF. Thereafter 16.38 g of freshly distillated triethoxysilane (HSi(OC$_2$H$_5$)$_3$) and about 2.5 to 3 mg of hexachloro-plantinic (IV) acid hexahydrate (40% Pt) were added. Due to the exothermic reaction the temperature of the solution increased to 30° C.

THF and surplus triethoxysilane were removed at an air bath temperature of 50° C. in vacuum (10 to 11 mbar). The distillate consisted of triethoxysilane. The raw product was concentrated for a further hour up to 55° C. in vacuum (0.8 to 1.0 mbar).

Yield: 16.02 g of raw product.

Coupling of the Silanized Eusolex® 9020-analogue to Monospher® 100

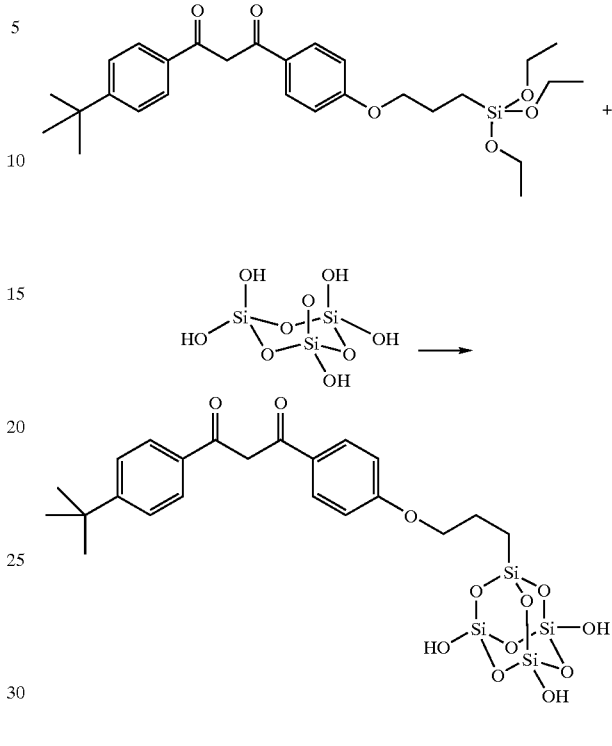

A 10% dispersion of 100 g of Monospher® 100 in about 1 l ethanol was heated to reflux temperature under a nitrogen blanket.

16.02 g of the silanized Eusolex® 9020 analogue were dissolved in 64 g of ethanol and introduced into a dropping funnel.

While being heated to boiling within a period of 70 minutes about 50% of the solution of silanized Eusolex® 9020 anaogue were dropped in. The obtained faintly yellowish dispersion was stirred for 5.5 hours under reflux. Thereafter the rest of the solution was added dropwise within 60 minutes. The reaction mixture was stirred overnight for 15 hours.

The dispersion was concentrated to a solid residue in a rotary evaporator. The residue then was dried for 68 hours at 40° C. in a vacuum exsiccator.

Yield: 106.99 of Eusolex® 9020/Monospher® 100-conjugate

Example 2

Preparation of a Eusolex® 9020/Monospher® 25-Conjugate

A Eusolex® 9020/Monospher® 25-conjugate was prepared according to the following reaction scheme:

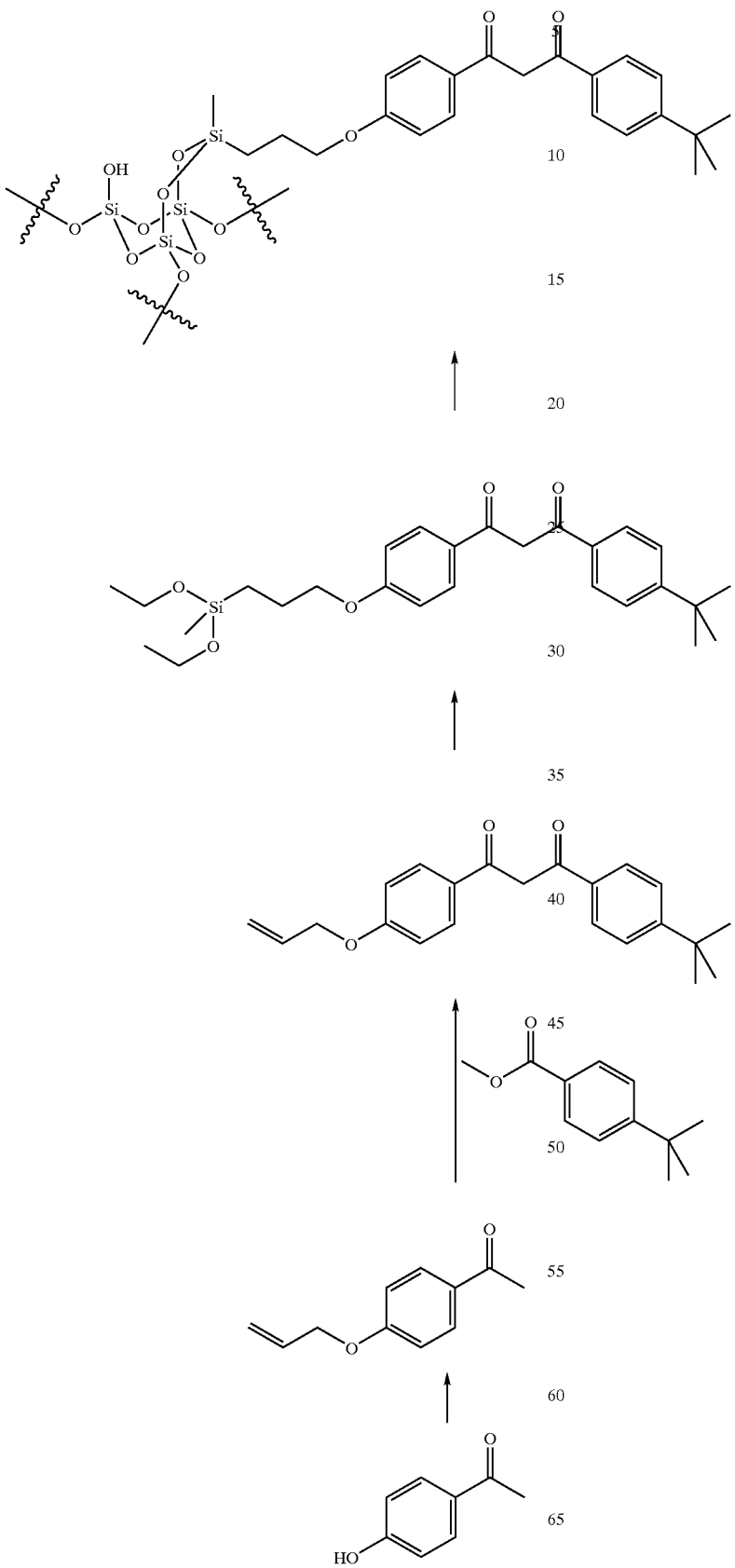

Preparation of 4-(2-propenyloxy)-acetophenone

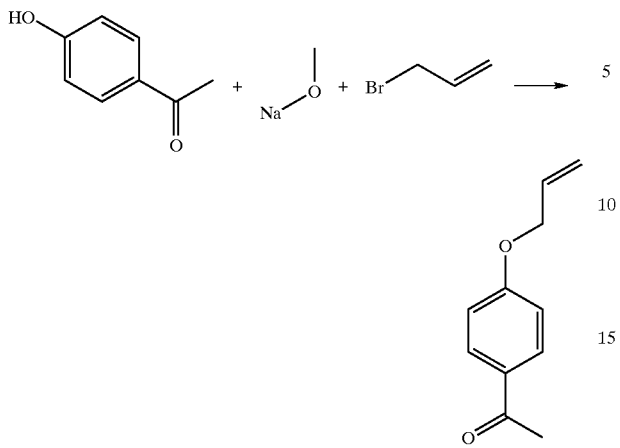

The apparatus used for carrying out the reaction was flushed with nitrogen to displace the air in the apparatus. Then 116 g of methanol and 16.67 g of 4-hydroxyacetophenone were introduced into the apparatus. The mixture was stirred until a homogeneous solution had been obtained. Then within 15 minutes 77.8 g of sodium methylate (30% solution in methanol) were added dropwise to obtain, after an exothermic reaction, a reddish solution. Thereafter the solution was heated to 56° C. and then within a period of 39 minutes 50.6 g of 3-bromo-1-propene were added dropwise, The reaction mixture was maintained for 21 hours at a temperature of from 63 to 65° C.

The yellow reaction solution was cooled to 40° C. and the methanol was removed in a rotary evaporator. The obtained partially crystalline concentrate was added with 200 g of toluene and 100 g of deionized water. Thereafter it was stirred for 5 minutes.

After the phase separation the organic phase was washed with 50 ml of a sodium hydroxide solution (1 molar) and twice with each 50 g of deionized water, filtered on absorbent cotton and then concentrated azeotropically in a rotary evaporator.

Yield: 60.9 g of raw product. 60.7 g of the raw product were fractional distilled in a 10 cm Vigreux column in vacuum (0.8 to 1.4 mbar). The period of distillaton was 3 hours. 50.89 g of 4-(2-propenyloxy)-acetophenone were obtained.

Preparation of a Eusolex® 9020 Analogue Capable to be Coupled

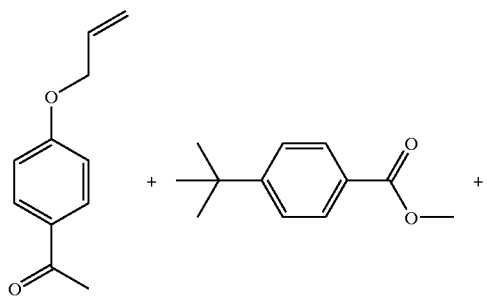

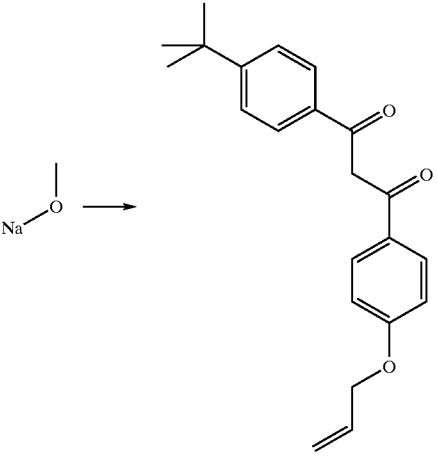

The apparatus used for carrying out the reaction was flushed with nitrogen to displaced the air in the apparatus. Then 764 g of cyclohexane were introduced and within 14 minutes heated to 50° C. Thereafter within 6 minutes 77 g of sodium methylate (30% solution in methanol) were added dropwise. The emulsion was heated to 64° C. and then within a period of 6 minutes a solution of 79.6 g of 4-t-butylbenzoic acid methylester in 100 g of cyclohexane was added dropwise. The reaction mixture was stirred for 70 minutes until a reaction temperature of 80° C. had been reached. During this period 220 ml of a cyclohexane/methanol mixture obtained in a water separator were removed in portions. Then within a period of 50 minutes a solution of 50.24 g of 4-(2-propenyloxy)acetophenone in 100 g of cyclohexane was added dropwise. During this period and in the following 4 hours 40 to 80 ml of the cyclohexane/methanol mixture (in a total of 400 ml) were removed in portions. The reaction temperature was 75 to 80° C. During the reaction three times each 120 g of cyclohexane were added dropwise. The reaction mixture was stirred for further 16 hours while the reaction temperature was maintained at 79.5 to 81° C.

Then the suspension was cooled to 70° C. and thereafter a mixture of 102.8 g of acetic acid (100%) and 85 g of deionized water was added dropwise and stirred for 40 minutes.

After the phase separation at 40° C. the organic phase was washed three times with each 50 ml of a sodium hydroxide solution (1 molar) and twice with 100 g and 50 g, respectively, of deionized water and then concentrated azeotropically to a redbrown oil in a rotary evaporator.

Yield: 115,7 g of raw product

The raw product was dissolved while heating in 145 g 2-propanol, filtered on absorbent cotton and cooled while stirring, After the addition of seed crystals a crystallization occurred (34° C.).

After stirring for 3 hours at 28° C. the suspension was slowly cooled to 10° C. within further 60 minutes. The crystallizate was isolated, washed with cold 2-propanol in portions and dried by suction. The drying was carried out in a vacuum exsiccator at 35° C.

Yield: 67.8 g of crystallizate (Eusolex® 9020 analogue capable to be coupled), melting point of the crystallizate: 66.8° C.

67.8 g of the crystallizate were dissolved in 156 g of 2-propanol while heating at 60° C. The solution was cooled while stirring. After the addition of seed crystals a crystallization occurred (44 to 45° C.).

After stirring for 2 hours at 26° C. the suspension was slowly cooled to 10° C. within further 60 minutes. The crystallizate was isolated, washed with cold 2-propanol in portions, dried by suction and dried at 35° C. in a vacuum exsiccator.

Yield: 65.0 g of crystallizate (melting point: 67.2° C.)

Preparation of a Silanized Eusolex® 9020-analogue

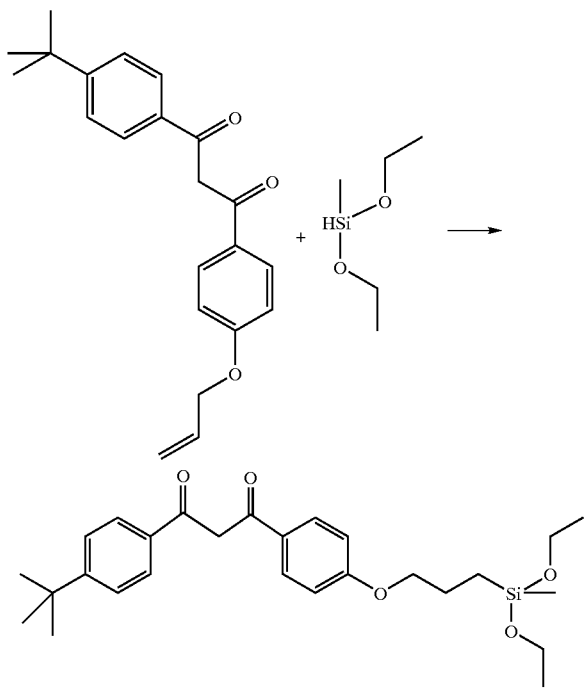

The apparatus used for carrying out the reaction was flushed with nitrogen to displace the air in the apparatus. Then 17.83 g of the crystallizate were dissolved in 9.6 g of THF in the apparatus. 14.82 g of methyidiethoxysilane (HSiCH$_3$(OC$_2$H$_5$)$_2$) and about 4 to 4.5 mg of hexachloroplatinic(IV) acid-hexahydrate (40% Pt) were added to the faintly yellowish solution. Due to an exothermic reaction the temperature of the solution increased to 30° C. The reaction mixture was stirred overnight.

THF and surplus methyidiethoxysilane were removed at an air bath temperature of 40° C. in vacuum (0.7 to 1.5 mbar). The raw product was degassed at the same temperature for further 0.75 hours.

Yield: 24.5 g of raw product.

Coupling of the Silanized Eusolex® 9020-analogue to Monospher® 25

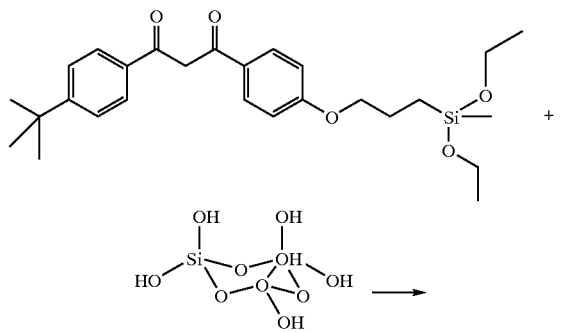

-continued

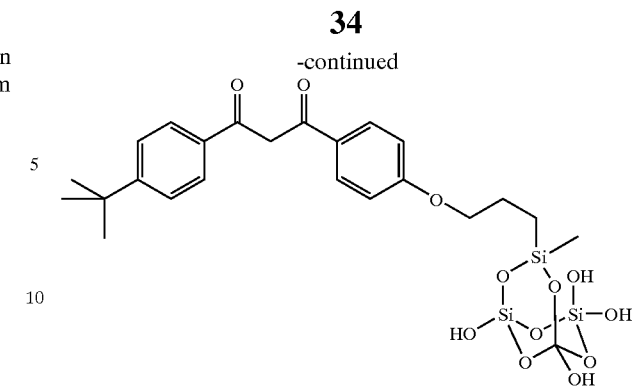

248.5 g of a dispersion of Monospher® 25 were concentrated in a rotary evaporator to 182 g by distilling off water, transferred into a 2 l-4-neck flask and filled up with 782 g of ethanol to a volume of about 1.2 l.

Via a distillation bridge within 8 hours 2530 g (about 3.15 to 3.2 l) of ethanol were distilled off. The volume of the dispersion was maintained by the addition of 2347 g of fresh ethanol (water content: 0.06%) by a dropping funnel.

From the flowing out distillate after each 1 l a sample was taken for determination of water (water content: 5.0; 1.8 and 1.0%).

After completion of the distillation the volume was concentrated to about 1000 ml.

The ethanolic dispersion of Monospher® 25 was heated unter reflux and a nitrogen blanket for silanizing it.

The silanized Eusolex® 9020 analogue was dissolved in 90 ml of ethanol, introduced into a dropping funnel and added dropwise within 6 hours while heating to boiling.

The reaction mixture was heated for 23 hours under reflux and thereafter stirred for 42 hours for cooling it.

Floating particles were removed by filtration on absorbent cotton and the dispersion (862 g) was concentrated in a rotary evaporator to a dry content of between 20 and 40%.

The reddish concentrate theoretically contains 99.7 g of Eusolex® 9020 bound to Monospher® 25. This corresponds to a dry content of 33.8%. The molar ratio between Eusolex® 9020 and Monospher® 25 is 96.24%: 3.76%.

Thereafter each 10 g of an ethanolic concentrate were transferred into a small round flask for test purposes, added with 7.88 g of the oils mentioned below and concentrated in a rotary evaporator until freeness of solvent, 11.26 g of dispersions having a dry solid content of 30% were expected to be obtained

| oil | trade name | yield (g) | content[1] (%) | consistency[2] |
|---|---|---|---|---|
| butyleneglycol-dicaprylate/di-caprinate | Miglyol 8810 | 11.70 | 28.9 | inhomogeneous solution |
| caprylic acid/caprinic acid triglycerides | Miglyol 812 neutral oil | 11.9 | 28.9 | inhomogeneous solution |
| butyleneglycol | 1.3-butanediol | 11.75 | 28.8 | solution/emulsion |
| coco acid glycerides | Myritol 331 | 12.00 | 28.2 | solution |
| C$_{12-15}$ alkyl-benzoate | Finsolv TN | 12.52 | 27.0 | inhomogeneous solution |

-continued

| oil | trade name | yield (g) | content[1] (%) | consistency[2] |
|---|---|---|---|---|
| octylpalmitate | Ceraphyl 368 | 12.06 | 28.0 | inhomogeneous solution |

[1]By residual ethanol the content decreases at an apparently higher dispersion yield.
[2]Refers to the dropwise addition of the oils to the ethanolic concentrate.

The major amount of the ethanolic concentrate (219.5 g) was transferred into a beaker flask and tempered in a rotary evaporator (water bath temperature; 50 to 55° C.). Within a period of from 12 to 15 minutes then 173 g of Finsolv TN were introduced.

The cloudy homogeneous dispersion was concentrated to a constant weight, meantime a clear "solution was formed".

Yield: 268 g of a yellow paste having a theoretical solid content of 74.2 g (27.7 5%) of Eusolex® 9020 bound to Monospher® 25.

Example 3

Preparation of a BHT/Monospher® 100-conjugate

A BHT/Monospher®100-conjugate was prepared according to the following reaction scheme.

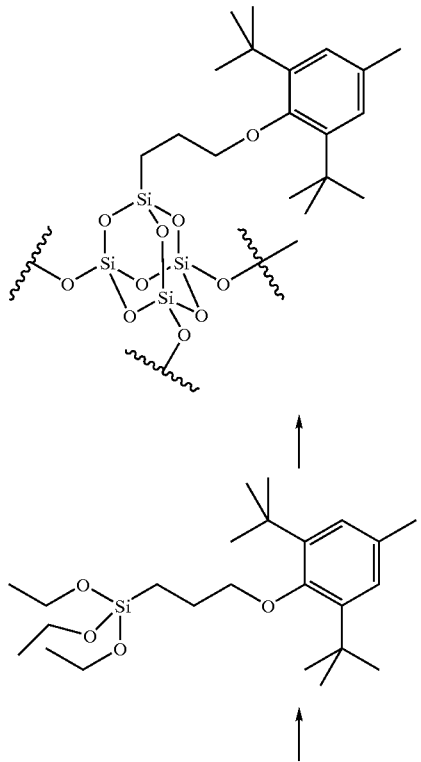

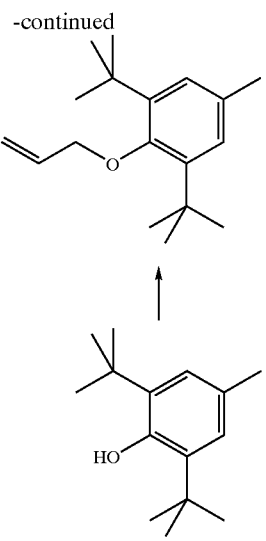

Preparation of 2,6-di-tert-butyl-4-methyl-1-(3-propen-1-yl-)oxy-benzene

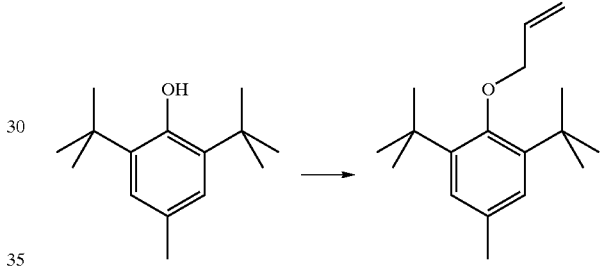

Analogously to the prescription of example 1 53 g of BHT (2,6-di-tert-butyl-4-methyl-phenol) were reacted with 35.5 g of 3-bromo-1-propene and 54 g of sodium methylate (30% solution in methanol).

After distillation in vacuum 46.8 g of 2,6-di-tert-butyl-4-methyl-1-(3-propene-1-yl-)oxy-benzene were obtained the physical data thereof were identical with the published data of the desired compound (CAS-No.: [1516-98-9]).

Preparation of the Silanized Intermediate Product

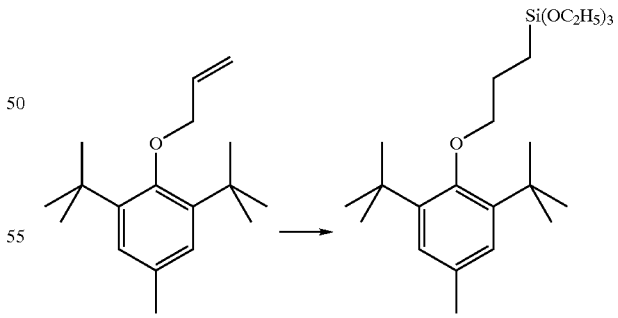

Analogously to the prescription of example 1 8.85 g of 2,6-di-tert-butyl-methyl-1-(3-propene-1-yl-)oxy-benzene in THF were reacted with 16.4 g of triethoxysilane. 2 mg of hexachloroplatinic(VI) acid hexahydrate were used as a catalyst.

14.8 g of raw product were obtained.

Coupling of the Silanized Intermediate Product to Monospher® 100

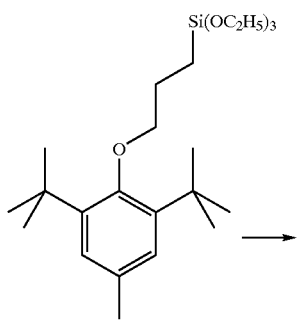

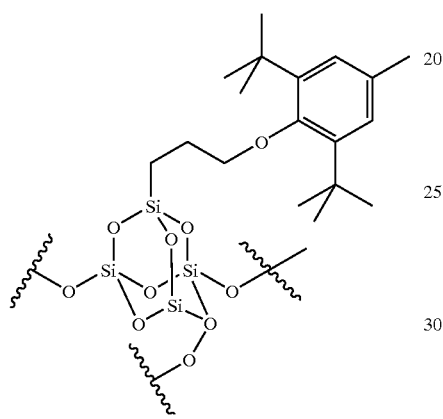

Analogously to the prescription of example 1 a 10% suspension of 100 g of Monospher® 100 in 1 l ethanol were reacted with the 14.8 g of raw product of the above synthesis.

Yield: 104,2 g of BHT/Monospher® 100-conjugate

Example 4

Preparation of a Methylparaben/Monospher® 25-conjugate

A Methylparaben/Monospher® 25conjugate was prepared according to the following reaction scheme:

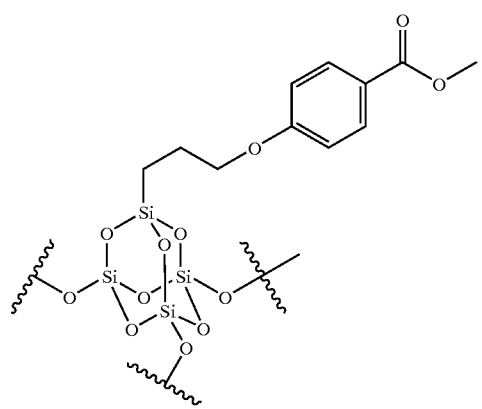

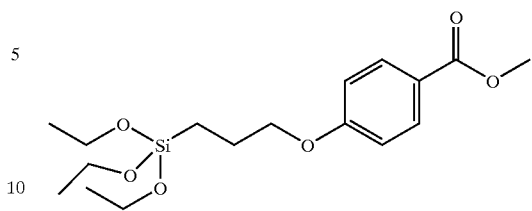

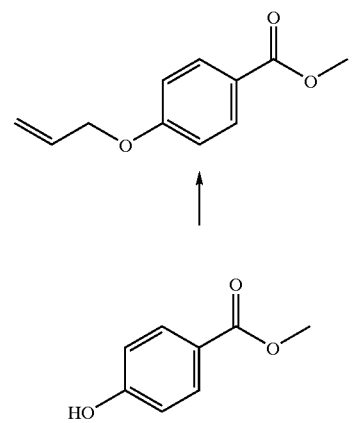

Preparation of 4-(3-propene-1-yl-)oxy-benzoic acid methylester

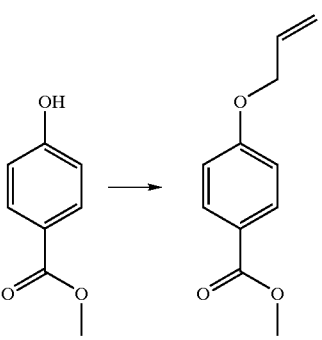

Analogously to the prescription of example 1 32 g of methylparaben (4-hydroxy-benzoic acid methylester) were reacted with 35.2 g of 3-bromo-1-propene and 54.5 g sodium methylate (30% solution in methanol).

After distillation in vacuum 37.6 g of 4-(3-propene-1yl-)oxy-benzoic acid methylester were obtained, the physical data thereof were identical to the published data of the desired compound (CAS-No.: [35750-24-4]).

Preparation of the Silanized Intermediate Product

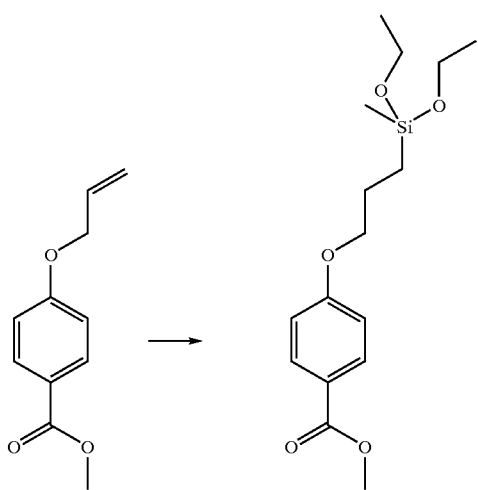

10.2 g of 4-(3-propene-1-yl-)oxy-benzoic acid methylester in THF were reacted with 14.8 g of methyldiethoxysilane analogously to the prescription of example 2.4 mg of hexachloroplatinic(VI) acid hexahydrate were used as a catalyst.

After the described reaction 17.7 g of raw product were obtained.

Coupling of the Silanized Intermediate Product to Monospher® 25

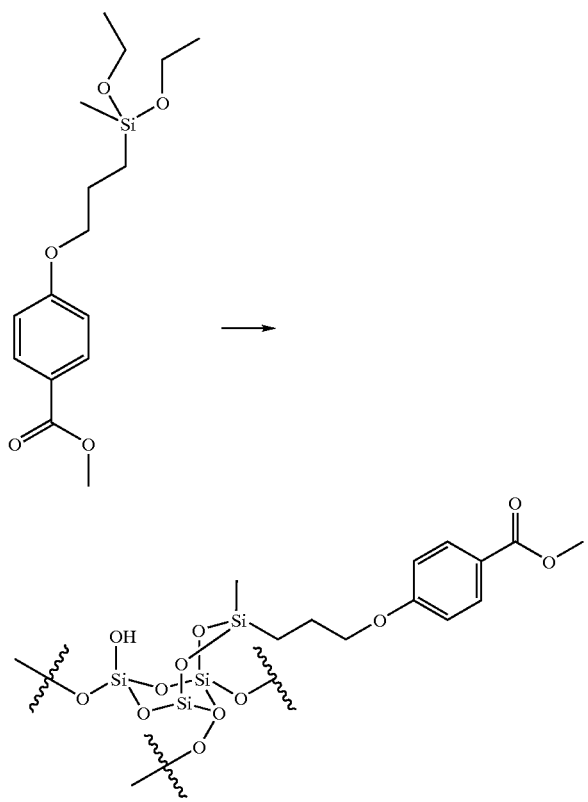

Analogously to the reaction described in example 2 an ethanolic suspension of about 80 g of Monospher® 25 was prepared and reacted with the 17.7 g of raw product (silylated methylparaben analogue) obtained in the above synthesis. The dispersion was concentrated in a rotary evaporator to a dry solid content of between 30% and 40% of conjugate.

For the preparation of cosmetic dispersions aliquots were added with the calculated amounts of various cosmetic oils (see table in example 2) and the ethanol was removed in a rotary evaporator.

In the following examples of skin and sun protection formulations the Eusolex® 9020/Monospher® 25-conjugate of example 2 was used. However, it is also possible to use the Eusolex® 9020/Monospher® 100-conjugate of example 1 or another conjugate of the invention.

Example 5

Examples of Skin Protection Formulations

| | raw material | INCI | | % by weight |
|---|---|---|---|---|
| | Skin protection lotion (O/W) | | | |
| A | Monospher-conjugate | | (1) | 5.00 |
| | Emulgator E 2155 | stearyl alcohol (and) Steareth-7 (and) Steareth-10 | (2) | 3.00 |
| | Teginacid H | glyceryl stearate (and) Cateth-20 | (2) | 3.00 |
| | Imwitor 900 | glyceryl stearate | (4) | 3.00 |
| | Lunacera M | microwax | (6) | 1.00 |
| | Luvitol EHO | cetearyl octanoate | (3) | 11.50 |
| | Cetiol | oleyl oleate | (5) | 6.00 |
| | Miglyol 812 neutral oil | caprylic/capric triglyceride | (4) | 6.00 |
| B | propanediol-1,2 | propylene gylcol | (1) | 4.0 |
| | allantoin | allantoin | (1) | 0.20 |
| | preservative | | | q.s. |
| | water, demineralized | aqua | ad | 100.00 |

Preparation

A phase A is heated to 75° C. and a phase B is heated to 80° C. The phase B is added to the phase A under slow stirring. The mixture is homogenized and cooled under stirring.

Remarks

Viscosity 9200 mPas (Brookfield RVT, Sp. C, 10 rpm) at 24° C.
pH 24° C.=5.0
preservative
  0.05% propyl-4-hydroxybenzoate
  0.15% methyl-4-hydroxybenzoate Supply Sources (1) Merck KGaA, Darmstadt
(2) Th. Goldschmidt, Essen
(3) BASF, Ludwigshafen
(4) Hüls, Troisdorf AG, Witten
(5) Henkel, Düsseldorf (6) H. B. Fuller GmbH, Lüneburg

| Skin protection lotion (O/W) | | | | |
|---|---|---|---|---|
| | raw material | INCI | | % by weight |
| A | Monospher-conjugate | | (1) | 1.00 |
| | Emulgator E 2155 | stearyl alcohol (and) Steareth-7 (and) Steareth-10 | (2) | 3.00 |
| | Teginacid H | glyceryl stearate (and) Cateth-20 | (2) | 3.00 |
| | Imwitor 900 | glyceryl stearate | (4) | 3.00 |
| | Lunacera M | microwax | (6) | 1.00 |
| | Luvitol EHO | cetearyl octanoate | (3) | 11.50 |
| | Cetiol | oleyl oleate | (5) | 7.00 |
| | Miglyol 812 neutral oil | caprylic/capric triglyceride | (4) | 7.00 |
| B | propanediol-1,2 | propylene gylcol | (1) | 4.00 |
| | allantoin | allantoin | (1) | 0.20 |
| | preservative | | | q.s. |
| | water, demineralized | aqua | ad | 100.00 |

Preparation

The phase A ist heated to 75° C. and the phase B is heated to 80° C. The phase B is slowly added under stirring to the phase A. The mixture is homogenized and cooled under stirring.

Remarks preservative:

0.05% propyl-4-hydroxybenzoate
0.15% methyl-4-hydroxybenzoate

Supply Sources (1) Merck KGaA, Darmstadt
(2) Th. Goldschmidt, Essen
(3) BASF, Ludwigshafen
(4) Hüls, Troisdorf AG, Witten
(5) Henkel, Düsseldorf
(6) H. B. Fuller GmbH, Lüneburg Example 6
Examples of Sun Protection Formulations

| Sun protection lotion containing IR3535 ™ (O/W) | | | | |
|---|---|---|---|---|
| | raw material | INCI | | % by weight |
| A | Monospher-conjugate | | (1) | 3.00 |
| | Eusolex 6300 | 4-methylbenzylidene camphor | (1) | 3.00 |
| | IR 3535 ™ | ethyl butylacetylaminopropionate | (1) | 10.00 |
| | (−)-α-bisabolol | bisabolol | (1) | 0.30 |
| | Montanov 68 | cetearyl alcohol (and) cetearyl glucosides | (2) | 4.00 |
| | Myritol 312 | caprylic/capric triglyceride | (3) | 2.00 |
| | Mirasil CM 5 | cyclomethicone | (4) | 2.00 |
| | Mirasil DM 350 | dimethicone | (4) | 1.00 |
| B | water, demineralized | aqua | ad | 100 |
| | glycerine, 87% | glycerine | (1) | 3.00 |
| | preservative | | | q.s. |
| C | Rhodicare S | xanthan gum | (4) | 0.50 |

Preparation

The phases A and B are separately heated to 75° C. The phase C is added slowly at 75° C. while stirring to the phase B. The mixture is stirred until it is homogeneous. Thereafter the phase A is added to the mixture. The mixture is stirred until it is homogeneous and then cooled while stirring.

Remarks preservative:

0.05% propyl-4-hydroxybenzoate
0.15% methyl-4-hydroxybenzoate
0.30% Germall 115 (ISP, Frechen)

Supply Sources (1) Merck KgaA, Darmstadt
(2) Interorgana, Köln
(3) Henkel, KgaA, Düsseldorf
(4) Rhodia, Frankfurt

| Sun protection milk (O/W) | | | | |
|---|---|---|---|---|
| | raw material | INCI | | % by weight |
| A | Monospher conjugate | | (1) | 4.00 |
| | Eusolex 6300 | 4-methylbenzylidene camphor | (1) | 4.00 |
| | Emulgator E 2155 | stearyl alcohol (and) Steareth-7 (and) Steareth-10 | (2) | 3.00 |
| | Teginacid H | glyceryl stearate (and) Cateth-20 | (2) | 2.00 |
| | Luvitol EHO | cetearyl octanoate | (3) | 14.00 |
| | Imwitor 900 | glyceryl stearate | (4) | 3.00 |
| | Cetiol | oleyl oleate | (5) | 6.00 |
| | Luncacera M | microwax | (6) | 1.00 |
| | Miglyol 812 neutral oil | caprylic/capric triglyceride | (4) | 4.00 |
| B | Eusolex 232 | phenylbenzimidazole sulfonic acid | (1) | 2.00 |
| | tris(hydroxymethyl)-aminomethane | tromethamine | (1) | 1.07 |
| | propanediol-1,2 | propylene glyocl | (1) | 4.00 |
| | allantoin | allantoin | (1) | 0.20 |
| | preservative | | | q.s. |
| | water, demineralized | aqua | ad | 100.00 |
| C | Carbopol ETD 2050 | Carbomer ETD 2050 | (7) | 0.25 |
| | water, demineralized | aqua | | 30.00 |
| D | Tris(hydroxymethyl)-aminomethane | tromethamine | (1) | 0.25 |
| | water, demineralized | aqua | | 4.00 |

Preparation

Carbopol ETD 2050 is dispersed homogeneously in water to obtain phase C. A phase D ist then introduced into phase C under homogenization. In order to neutralize Eusolex 232 the tris(hydroxymethyl)-aminomethane is dissolved in the water of phase B and Eusolex 232 is added under stirring, After completion of dissolution the residual ingredients of phase B are added and phase B is slowly introduced into phases C/D under homogenization. Phase A is dissolved by heating and is slowly added under homogenization.

Remarks

Preservative:

0.05% propyl-4-hydroxybenzoate
0.15% methyl-4-hydroxybenzoate

Supply Sources (1) Merck KGaA, Darmstadt
(2) Th. Goldschmidt, Essen
(3) BASF, Ludwigshafen
(4) Hüls, Troisdorf AG, Witten
(5) Henkel, Düsseldorf
(6) H. B. Fuller GmbH, Lüneburg (7) Goodrich, Neuss

| | Sun protection lotion (W/O) | | |
|---|---|---|---|
| | raw material | | % by weight |
| A | Monospher conjugate | (1) | 5.00 |
| | Eusolex HMS | (1) | 5.00 |
| | Eusolex OS | (1) | 5.00 |
| | Eusolex OCR | (1) | 5.00 |
| | Abil WE 09 | (2) | 5.00 |
| | Jojoba oil | (3) | 3.00 |
| | Cetiol V | (4) | 3.00 |
| | Prisorine 2021 | (5) | 2.00 |
| | Lunacera M | (6) | 1.80 |
| | Miglyol 812 neutral oil | (7) | 3.00 |
| B | glycerine (about 87%) | (1) | 2.00 |
| | sodium chloride | (1) | 0.40 |
| | preservative | (1) | q.s. |
| | water, demineralized | ad | 100.00 |

Preparation

Phase B ist heated to 80° C. and phase A is heated to 75° C. Phase B is slowly introduced into phase A under stirring. The mixture ist homogenized and cooled while stirring.

Remarks

Preservative:
  0.05% propyl-4-hydroxybenzoate
  0.15% methyl-4-hydroxybenzoate

Supply Sources (1) Merck KGaA, Darmstadt
(2) Th. Goldschmidt AG, Essen
(3) H. Lamotte, Bremen
(4) Henkel KGaA, Düsseldorf
(5) Unichema, Emmerich
(6) H. B. Fuller, Lüneburg
(7) Hüls Troisdorf AG, Witten

| | Sun protection cream (W/O) | | |
|---|---|---|---|
| | raw material | INCI | % by weight |
| A | Monospher conjugate | | (1) 2.50 |
| | Eusolex T-2000 | micron. titanium dioxide | (1) 2.50 |
| | Eusolex 6300 | 4-methylbenzylidene camphor | (1) 2.00 |
| | Dehymuls E | dicocoyl pentaerythrityl citrate (and) sorbitan sesquioleate (and) cera alba (and) aluminum stearate | (2) 6.00 |
| | Arlacel 989 | PEG-7 hydrogenated castor oil | (3) 1.00 |
| | beeswax | cera alba | (1) 2.00 |
| | zinc stearate | zinc stearate | (1) 2.00 |
| | Cetiol J 600 | oleyl erucate | (2) 6.00 |
| | Cetiol V | decyl oleate | (2) 6.00 |
| | Cetiol OE | dicaprylyl ether | (2) 5.00 |
| | Dow Corning 200 (100 cs) | dimethicone | (4) 1.00 |
| | DL-α-tocopherol-acetate | tocopheryl acetate | (1) 1.00 |
| | Vitamin A palmitate | retinyl palmitate | (5) 0.50 |
| B | Eusolex 232 | phenylbenzimidazole sulfonic acid | (1) 2.00 |
| | tris(hydroxymethyl)-aminomethane | tromethamine | (1) 0.88 |
| | glycerine (about 87%) | glycerine | (1) 5.00 |
| | magnesium sulfate | magnesium sulfate | (1) 1.00 |
| | heptahydrate | | |
| | allantoin | allantoin | (1) 0.20 |
| | preservative | | q.s. |
| | water, demineralized | | ad 100.00 |

Preparation

In order to neutralize Eusolex 232 the tris (hydroxymethyl)-aminomethane is dissolved in the water of phase B and Eusolex 232 is added while stirring. After complete dissolution the residual raw materials of phase B are added and heated to 80° C. Phase A is heated to 75° C. Phase B is slowly added to phase A while stirring and the mixture is cooled while stirring.

Remarks

Preservative:
  0.05% propyl-4-hydroxybenzoate
  0.15% methyl-4-hydroxybenzoate

Supply Sources (1) Merck KGaA, Darmstadt
(2) Henkel KGaA, Düsseldorf
(3) ICI, Essen
(4) Dow Corning, Düsseldorf
(5) Hoffmann La Roche, Schweiz

| | Sun protection gel (O/W) exhibiting UV-A/B screen | | |
|---|---|---|---|
| | raw material | | % by weight |
| A | Monospher conjugate | (1) | 2.00 |
| | Eusolex 2292 | (1) | 5.50 |
| | Oxynex K liquid | (1) | 1.00 |
| | Luvitol EHO | (2) | 9.00 |
| | Dow Corning 200 (100 cs) | (3) | 2.00 |
| | Antaron V-220 | (4) | 2.00 |
| | jojoba oil | (5) | 5.00 |
| B | tris(hydroxymethyl) aminomethane | (1) | 0.60 |
| | preservative | | q.s. |
| | water, demineralized | ad | 100.00 |
| C | Pemulen TR-1 | (6) | 0.50 |
| | water, demineralized | | 29.50 |
| D | Aloe Vera gel 1:10 | (7) | 1.00 |

Preparation

PemulenTR-1 is dispersed homogeneously in water and preswelled to obtain phase C. Phase B is introduced into phase C under homogenization. Phase A is dissolved by heating and added slowly under homogenization. Phase D is added at 35° C. and again homogenized.

Remarks

Preservative:
  0.05% propyl-4-hydroxybonzoate
  0.15% methyl-4-hydroxybenzoate

Supply Sources (1) E. Merck, Darmstadt
(2) BASF, Ludwigshafen
(3) Dow Corning, Düsseldorf (4) GAF, Frechen
(5) Henry Lamotte, Bremen
(6) Goodrich, Neuss
(7) Galke, Gittelde

| Sun protection spray (O/W) | | | |
|---|---|---|---|
| raw material | INCI | | % by weight |
| A Monospher conjugate | | (1) | 3.00 |
| Eusolex 2292 | octyl methoxycinnamate | (1) | 7.50 |
| Eusolex HMS | homosalate | (1) | 7.00 |
| Volpo S-2 | Steareth-2 | (2) | 0.40 |
| Volpo S-10 | Steareth-10 | (2) | 0.80 |
| Pemulen TR-2 | Acrylate/$C_{10-30}$-alkyl acrylate crosspolymer | (3) | 0.18 |
| Hetester PHA | propylene glycol isoceteth-3 acetate | (4) | 5.00 |
| Performa V 825 | synthetic wax | (5) | 0.80 |
| Dow Corning 200 (100 cs) | dimethicone | (6) | 1.00 |
| Oxynex K liquid | PEG-8 (and) tocopherol (and) ascorbyl palmitate (and) ascorbic acid (and) citric acid | (1) | 0.10 |
| B Eusolex 232 | phenylbenzimidazole sulfonic acid | (1) | 1.00 |
| triethanolamine | triethanolamine | (1) | 0.90 |
| propanediol-1,2 | propylene glycol | (1) | 2.00 |
| preservative | | | q.s. |
| water, demineralized | aqua | ad | 100.00 |

Preparation

In order to neutralize Eusolex 232 triethanolamine is added to the water of phase B and Eusolex 232 is added while stirring. After complete dissolution the residual raw materials of phase B are added and heated to 80° C. Phase A is added with the exception of Pemulen and heated to 80° C. Then Pemulen is added to phase A while stirring. Phase B is slowly added to phase A while stirring and the mixture is homogenized and cooled while stirring.

Remarks

Preservative:
  0.05% propyl-4-hydroxybenzoate
  0.15% methyl-4-hydroxybenzoate

Supply Sources (1) Merck KGaA, Darmstadt
(2) Croda, Nettetal
(3) Goodrich, Neuss
(4) ROVI, Schlüchtern
(6) New Phase, NJ 08554
(6) Dow Corning, Wiesbaden

What is claimed is:

1. A conjugate, comprising an inorganic pigment and an active substance based on organic compounds being covalently bound through a spacer group to the inorganic pigment, characterized in that the spacer group contains a silicon atom or an aluminum atom.

2. The conjugate according to claim 1, wherein the inorganic pigment is a metal or semi-metal compound.

3. The conjugate according to claim 2, wherein the metal or semi-metal compound is an oxide, silicate, phosphate, carbonate, sulfate or nitride.

4. The conjugate according to claim 3, wherein the oxide is magnesium oxide, aluminum oxide, silicon oxide, zinc oxide, cerium oxide, titanium oxide, zirconium oxide, manganese oxide, boron oxide, iron oxide or a mixture of these oxides.

5. The conjugate according to claim 3, wherein the oxide is present in the form of spherical monodisperse oxide particles.

6. The conjugate according to claim 3, wherein the silicate is a mica or a talc.

7. The conjugate according to claim 1, characterized by a particle size of from 1 nm to 250 µm.

8. The conjugate according to claim 1, wherein the active substance is a compound selected from light absorbing organic compounds, substances having antioxidative and/or radical inhibiting properties, repellants, preservatives and derivatives of these active substances.

9. The conjugate according to claim 8, wherein the light absorbing organic compound is selected from derivatives of aminobenzoic acid, cinnamic acid, salicylic acid, benzylidene camphor, phenylbenzimidazole, diphenylacrylate, triazine, triazole, benzophenone, benzoylmethane, diarylbutadienes and vinyl group-containing amides.

10. The conjugate according to claim 9, wherein the light absorbing organic compound is photostable.

11. The conjugate according to claim 8, wherein the substances having antioxidative and/or radical inhibiting properties are selected from flavonoides, coumaranones, vitamins and BHT.

12. The conjugate according to claim 8, wherein the repellants are selected from amides and derivatives thereof.

13. The conjugate according to claim 12, wherein the repellants are selected from N,N-diethyl-3-methylbenzamide, 3-[N-n-butyl-N-acetyl]-aminopropionic acid ethyl ester and N,N-caprylic acid diethylamide.

14. The conjugate according to claim 8, wherein the preservatives are selected from benzalkonium chloride, benzoic acid and salt thereof, methylparaben, ethylparaben, propylparaben, sorbic acid and salts thereof, cetylpyridinium chloride, cetrimonium chloride and salicylic acid and salts thereof.

15. The conjugate according to claim 1, comprising the general formula

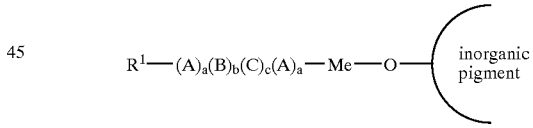

wherein:

$R^1$ is the covalently bound reactive substance-group

A represents O, S or NH,

B represents a straight or branched alkylene group having up to 20 carbon atoms, C represents a straight or branched alkyleneoxy group having up to 20 carbon atoms, wherein the oxygen atom of the alkyleneoxy group is bound to group B, Me represents a silicon atom or an aluminum atom a is 0 or 1, b is 0 or 1, c is 0 or 1, wherein the silicon atom and aluminum atom, respectively is capable to form one or more covalent bonds to the inorganic pigment and/or to the active substance group.

16. The conjugate according to claim 15, characterized in that $R^1$ is selected from the group consisting of
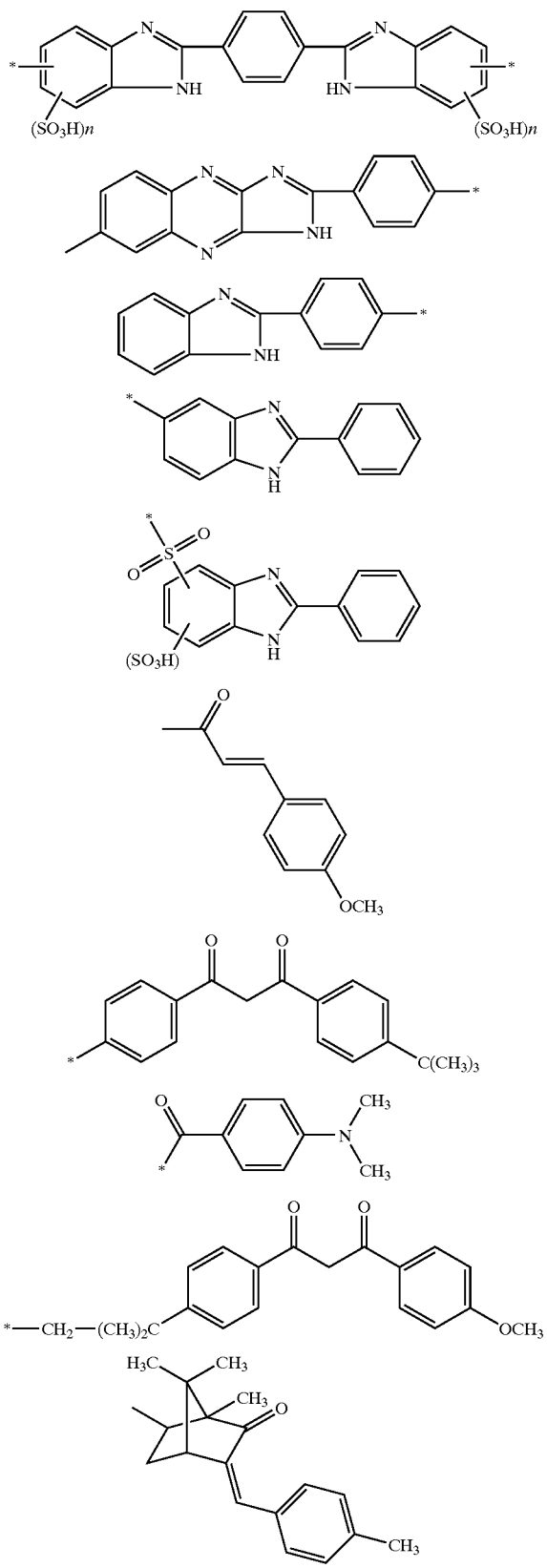
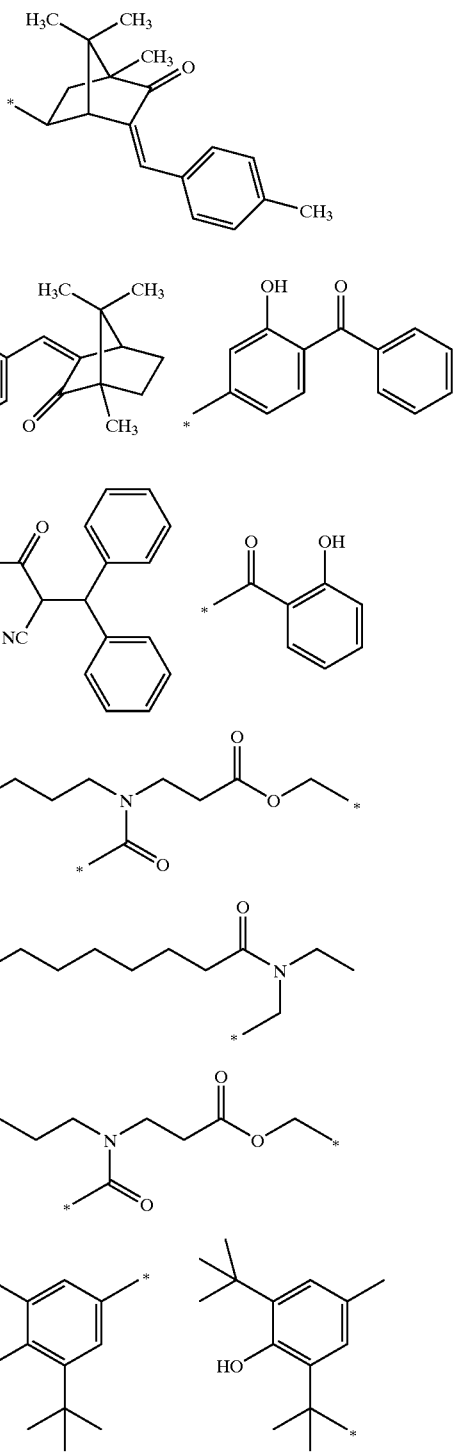
wherein n is 0, 1 or 2 and * represents the bond to the spacer group.
17. The conjugate according to claim 1, wherein the active substance is soluble in water and/or soluble in oil.

18. A conjugate of the formula

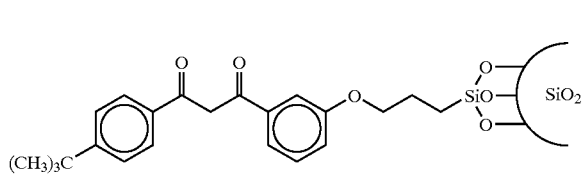

wherein $SiO_2$ is a pigment based on silicon dioxide.

19. A conjugate of the formula

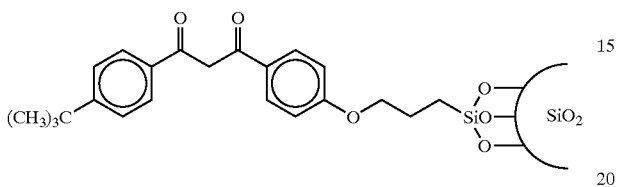

wherein $SiO_2$ is a pigment based on silicon dioxide.

20. A conjugate of the formula

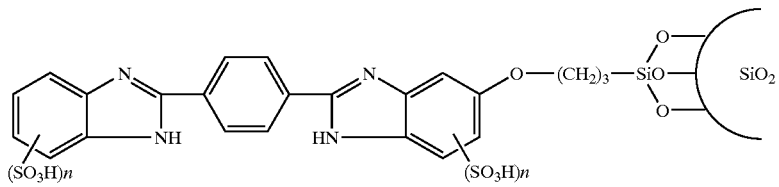

wherein $SiO_2$ is a pigment based on silicon dioxide and n is 0, 1 or 2.

21. A conjugate of the formula

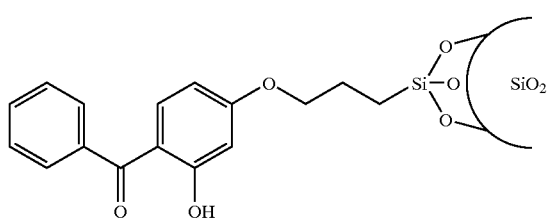

wherein $SiO_2$ is a pigment based on silicon dioxide.

22. A conjugate of the formula

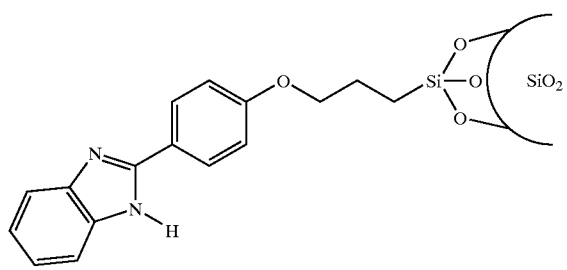

wherein $SiO_2$ is a pigment based on silicon dioxide.

23. A conjugate of the formula

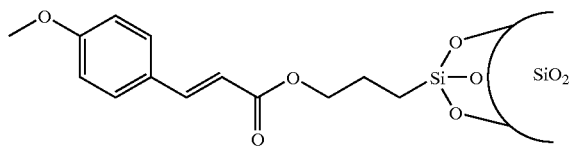

wherein $SiO_2$ is a pigment based on silicon dioxide.

24. A conjugate of the formula

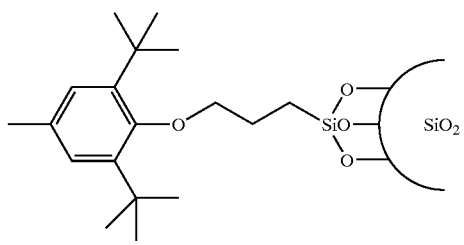

wherein $SiO_2$ is a pigment based on silicon dioxide.

25. A conjugate of the formula

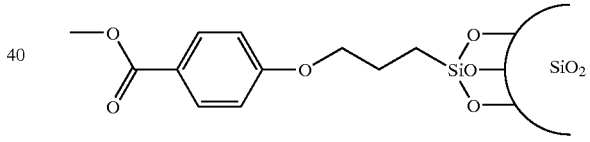

wherein $SiO_2$ is a pigment based on silicon dioxide.

26. A dermatological or cosmetic composition comprising at least one conjugate according to claim 1 and at least one cosmetically, pharmaceutically and/or dermatologically compatible vehicle and/or adjuvant.

27. The dermatological or cosmetic composition according to claim 26, wherein it contains at least one further UV protecting substance.

28. The dermatological or cosmetic composition according to claim 26, wherein it contains an antioxidant.

29. A dispersion, comprising a conjugate according to claim 1, and an oil ingredient and/or a liquid light filter.

30. A process for preparing the conjugate according to claim 1, the process comprising:

(a) reacting a compound having at least two terminal reactive groups with an active substance based on organic compounds to bind covalently both compounds to each other through one of both reactive groups, and (b) subsequently reacting the compound obtained in step (a) with an inorganic pigment in order to covalently bind the compound obtained in step (a) through the other reactive group to an inorganic pigment.

31. The process for preparing the conjugate according to claim 1, the process comprising:
   (a) reacting a compound having at least two terminal reactive groups with an inorganic pigment in order to bind covalently the compound to the pigment through one of both reactive groups, and
   (b) subsequently reacting the compound obtained in step (a) with an active substance based on organic substances in order to bind covalently the compound obtained in step (a) through the other reactive group to the active substance.

32. Use of the conjugate according to claim 1 for preparing a sun protection formulation or a skin protection formulation.

33. Use of the conjugate according to claim 1 for protecting skin cells.

34. The use according to claim 33 for protecting the Langerhans cells in the skin.

35. Use of the conjugate according to claim 1 for protecting the DNA.

36. Use of the conjugate according to claim 1 for immunoprotection.

* * * * *